(12) United States Patent
Ochiai et al.

(10) Patent No.: US 8,247,209 B2  
(45) Date of Patent: Aug. 21, 2012

(54) GLYCEROL-3-PHOSPHATE ACYLTRANSFERASE (GPAT) HOMOLOGS AND USE THEREOF

(75) Inventors: Misa Ochiai, Osaka (JP); Hisanori Tokuda, Osaka (JP)

(73) Assignee: Suntory Holdings Limited, Osaka (JP)

( * ) Notice: Subject to any disclaimer, the term of this patent is extended or adjusted under 35 U.S.C. 154(b) by 132 days.

(21) Appl. No.: 12/515,834

(22) PCT Filed: Jun. 12, 2008

(86) PCT No.: PCT/JP2008/060789  
§ 371 (c)(1), (2), (4) Date: May 21, 2009

(87) PCT Pub. No.: WO2008/156026  
PCT Pub. Date: Dec. 24, 2008

(65) Prior Publication Data  
US 2010/0159110 A1    Jun. 24, 2010

(30) Foreign Application Priority Data  
Jun. 18, 2007 (JP) .................. 2007-160042

(51) Int. Cl.  
*C12N 1/20* (2006.01)  
*C12N 15/11* (2006.01)

(52) U.S. Cl. ........... 435/252.3; 435/320.1; 435/183; 435/200; 536/23.1; 536/23.2

(58) Field of Classification Search .......... None  
See application file for complete search history.

(56) References Cited

U.S. PATENT DOCUMENTS

| | | | |
|---|---|---|---|
| 6,160,203 A * | 12/2000 | Ferri et al. .................. 800/281 |
| 7,192,762 B2 | 3/2007 | Macool et al. | |
| 2006/0115881 A1 | 6/2006 | Damude et al. | |
| 2006/0174376 A1 | 8/2006 | Renz et al. | |

FOREIGN PATENT DOCUMENTS

| | | |
|---|---|---|
| WO | 2004/087902 | 10/2004 |
| WO | 2006/052824 | 5/2006 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Mishra et al., "Purification and Characterization of Thiol-Reagent-Sensitive Glycerol-3-Phosphate Acyltransferase from the Membrane Fraction of an Oleaginous Fungus," Biochem. J., (2001) vol. 355, pp. 315-322.

Chatrattanakunchai et al., "Oil Biosynthesis in Microsomal Membrane Preparations from *Mortierella alpina*," Biochem. Soc. Trans., (2000) vol. 28, pp. 707-709.

Fraser et al., "Kinetic Analysis of Microsomal *SN*-Glycerol-3-Phosphate Acyltransferase from the Developing Seeds of Sunflower and *Mortierella alpina*," Adv. Res. Plant Lipids Proc. Int. Symp., (2003) pp. 187-190.

Zheng et al., "The Initial Step of the Glycerolipid Pathway," J. Biol. Chem., (2001) vol. 276, No. 45, pp. 41710-41716.

Dircks et al., "Mammalian Mitochondria Glycerol-3-Phosphate Acyltransferase," Biochim. Biophys. Acta, (1997) vol. 1348, pp. 17-26.

Murata et al., "Glycerol-3-Phosphate Acyltransferase in Plants," Biochim. Biophys. Acta, (1997) vol. 1348, pp. 10-16.

XP002660985.  
XP002660986.  
XP002660987.  
Extended European Search Report dated Oct. 20, 2011.

* cited by examiner

*Primary Examiner* — Richard Hutson  
(74) *Attorney, Agent, or Firm* — Greenblum & Bernstein, P.L.C.

(57) ABSTRACT

The present invention provides novel genes for glycerol-3-phosphate acyltransferase. In exemplary embodiments, the invention provides a nucleic acid comprising the nucleotide sequence shown in SEQ ID NO: 1 or 4 or a fragment thereof.

4 Claims, 1 Drawing Sheet

```
   1  GCTTCCCTCCACACTTCCCTTTCCTTCAACACCAAACCCTATCCGAACCCTCTGTCTCATTTTTCTCTCTCTCTCCCTATCTCTCTCTCTCTATCCTC

101  ACATATATCCTCATGGCCAAACTTCGGAAGCGGACCTCCCAGTCAAAGGAGGGCGCCGCTGACACCAACGGCACAAGGCGAGACAGCGTCGATGACACGA
           M  A  K  L  R  K  R  T  S  Q  S  K  E  G  A  A  D  T  N  G  T  R  R  D  S  V  D  D  T  N  ·

201  ACAGCGTCGGCAGCTACGATCCACGCGCCCTCTCCAACGATCCACCAAAGATGTACAGGGCGATCCGGTTCTTCTTCAAGATGTGCCTGCACTCCTTCTA
      ·  S  V  G  S  Y  D  P  R  A  L  S  N  D  P  P  K  M  Y  R  A  I  R  F  F  F  K  M  C  L  H  S  F  Y  ·

301  TGGCCATGTGGAGGTCGAGGGCACCGAGAATATTGCACCAAACAACTACCCTGCTATCCTTGTTGCGAACCACACAGCAACAGTTTGACGGATGCGATTGCC
      ·  G  H  V  E  V  E  G  T  E  N  I  A  P  N  N  Y  P  A  I  L  V  A  N  H  S  N  S  L  T  D  A  I  A
                                                                                   *                    *

401  ATTATGTCGACTCTTCCTCCCAAGAGCAGGAGCATGATTAGGATGACCGCAAAGGACACGTTTTGGCATAAGCCAGGCGTCTTCAATTATGTCATCAAAA
         I  M  S  T  V  P  P  K  S  R  S  M  I  R  M  T  A  K  D  T  F  W  H  K  P  G  V  F  N  Y  V  I  K  N  ·

501  ACGCTGGCACTGTCCCGATCAAAAGACGCAAGGATTATGAGAACCAAAAGGTCGACAACACTGACGCGATGGGTGCATTGATCGATACCCTTGGAGCAGG
         ·  A  G  T  V  P  I  K  R  R  K  D  Y  E  N  Q  K  V  D  N  T  D  A  M  G  A  L  I  D  T  L  G  A  G  ·
                                +

601  AAGTTGTGTATGCATGTTCCCGGAGGGCATCTCGCGCTATCACCCACAACTTGCTCCGTTCAAGGCCGGTGTCGCCATGATTGCCAGCGATACGCTCTCC
         ·  S  C  V  C  M  F  P  E  G  I  S  R  Y  H  P  Q  L  A  P  F  K  A  G  V  A  M  I  A  S  D  T  L  S
                *        +

701  CGGTTTCAAGACACGCCCGATTTTCTCTCACGCTCATGACAGCGTCGATCAACTATCTTCACCGTGAAAAGTTCCGATCTGATGTTCTCGTCACGTTCC
         R  F  Q  D  T  P  D  F  S  L  T  L  M  T  A  S  I  N  Y  L  H  R  E  K  F  R  S  D  V  L  V  T  F  H  ·

801  ATGCACCCATTGTGCTAACCCCGCAACAAGACTCGAAGCTGTTTTCGACTGACCTGGAAGTCAAGAAGGAAGCGATCCGAAAACTGACAGAGTTGCTCGA
         ·  A  P  I  V  L  T  P  Q  Q  D  S  K  L  F  S  T  D  L  E  V  K  K  E  A  I  R  K  L  T  E  L  L  E  ·

901  GGGCACCGTCCGATCAACTCTACTGGATGCCGAGGACTGGCAAACAGTCCGAGTGGGTCATGTTGCCAGGAAGCTCTATGCTGGCGATCTGGGAACTCGG
         ·  G  T  V  R  S  T  L  L  D  A  E  D  W  Q  T  V  R  V  G  H  V  A  R  K  L  Y  A  G  D  L  G  T  R

1001  ATTTCGCTGGGACAGTACGTGCGTTTGACCAGGAAGTTTGTCACGGCGTTCAGTCAGCACAAGCAGGAGGAGGAGGCAGCGGTCGATGACGAGCGTTATG
         I  S  L  G  Q  Y  V  R  L  T  R  K  F  V  T  A  F  S  Q  H  K  Q  E  E  E  A  A  V  D  D  E  R  Y  G  ·

1101  GTCAGGAGAAGCACGGGGGCGGTGCCGAGAGGAATGGTGATTCTTTGGAGATGAGGCATCCTGAGCGCATGGATAAGGCGACTAGAAAGAAAATCGACGA
         ·  Q  E  K  H  G  G  G  A  E  R  N  G  D  S  L  E  M  R  H  P  E  R  M  D  K  A  T  R  K  K  I  D  E  ·

1201  GCTCGCCAGGGATTTGGCTGACTACCAAAACCAGCTGGACTTCTATCACCTCAAGGACTATCGTATCAAGCAAGGCAAGCCAAGTGCAAAGATTCTTATC
         ·  L  A  R  D  L  A  D  Y  Q  N  Q  L  D  F  Y  H  L  K  D  Y  R  I  K  Q  G  K  P  S  A  K  I  L  I

1301  GGACGTCTTTTCCAAAGATTCTTGCTTGCTTGCCTTTTGTCGACCATTTGCATTCCTGGACTGTTCCTTTGGGCACCTGTGTTTATCGCCGTGAAGTACA
         G  R  L  F  Q  R  F  L  L  A  C  L  L  S  T  I  C  I  P  G  L  F  L  W  A  P  V  F  I  A  V  K  Y  K  ·

1401  AAGAGAGTCAGCTTAGGCGCAAGGGACCCTTGGAGGACAACTTGGATGAAATTGCCCAGTACAAGTTGATGATCTCGACTTTCTTCTTGCCGATCATCTG
         ·  E  S  Q  L  R  R  K  G  P  L  E  D  N  L  D  E  I  A  Q  Y  K  L  M  I  S  T  F  F  L  P  I  I  W  ·

1501  GGGGTTCTGGATCGTAATGACCTTGCCAATTGCGCTCTTTAGCGCGCCGGGCATCGTTGTTCTGATGTGGCTTACGATCCGCTGGCTTGAGGACTTGATC
         ·  G  F  W  I  V  M  T  L  P  I  A  L  F  S  A  P  G  I  V  V  L  M  W  L  T  I  R  W  L  E  D  L  I

1601  CACAACGCGAAATCGATGTTGTCCCTTTTGCGATTGCTGTTTATGACGGAGGATACCATGTACTCGTTGAGAGACTACCGTCAGGGGCTGGCGCATCGTG
         H  N  A  K  S  M  L  S  L  L  R  L  L  F  M  T  E  D  T  M  Y  S  L  R  D  Y  R  Q  G  L  A  H  R  V  ·

1701  TGCACGATTTTGCGGTCGATCATCTGAAGTTGCCTGAGGACCCTGAGGTTCTGGTCAAGGAGAACAAGACCAAGAAGGTCGACAGTGGCTGGATGGGCAA
         ·  H  D  F  A  V  D  H  L  K  L  P  E  D  P  E  V  L  V  K  E  N  K  T  K  K  V  D  S  G  W  M  G  K  ·

1801  GTTGTCGGGCAGCTACTTCTCGATCAAGAGGAGAAGAAGAAAGGACTGGAACGAGGTTATGCGATTGCACGATGTTTCTCACTATGACTGAAGCTGAGAT
         ·  L  S  G  S  Y  F  S  I  K  R  R  R  R  R  K  D  W  N  E  V  M  R  L  H  D  V  S  H  Y  D

1901  CGTCCTTGAATAAAAGCAGATAACGCGTGGAGTAACTGAGGG
```

GLYCEROL-3-PHOSPHATE ACYLTRANSFERASE (GPAT) HOMOLOGS AND USE THEREOF

TECHNICAL FIELD

The present application claims priority to Japanese Patent Application No. 2007-160042 (filed on Jun. 18, 2007).

The present invention relates to novel genes for glycerol-3-phosphate acyltransferase.

BACKGROUND ART

Fatty acids are important components of lipids such as phospholipids and triacylglycerols. Fatty acids containing two or more unsaturated bonds are collectively referred to as polyunsaturated fatty acids (PUFA) and are known to include arachidonic acid, dihomo-γ-linolenic acid, eicosapentaenoic acid and docosahexaenoic acid. Various physiological activities have been reported for these fatty acids (Non-patent Document 1). These polyunsaturated fatty acids are expected to have applications in various fields, but some of them cannot be synthesized in the animal body. Thus, microbial techniques have been developed for obtaining polyunsaturated fatty acids by culturing various microorganisms. Other attempts have also been made to produce polyunsaturated fatty acids in plants. In these cases, polyunsaturated fatty acids are known to be accumulated, for example, as components of storage lipids such as triacylglycerols within microorganism cells or plant seeds.

More specifically, triacylglycerols are produced in vivo as follows. Namely, glycerol-3-phosphate is acylated by glycerol-3-phosphate acyltransferase to form lysophosphatidic acid, which is then acylated further by lysophosphatidic acid acyltransferase to form phosphatidic acid. This phosphatidic acid is, in turn, dephosphorylated by phosphatidic acid phosphatase to form diacylglycerol, which is then acylated by diacylglycerol acyltransferase to form triacylglycerol. Other enzymes such as acylCoA:cholesterol acyltransferase and lysophosphatidylcholine acyltransferase are also known to be indirectly involved in biosynthesis of triacylglycerols.

In the above pathway of triacylglycerol biosynthesis or in the pathways of phospholipid biosynthesis, the reaction in which glycerol-3-phosphate is acylated to form lysophosphatidic acid is known to be mediated by glycerol-3-phosphate acyltransferase (hereinafter also referred to as "GPAT"; EC 2.3.1.15).

GPAT genes have been reported so far in several organisms. As mammalian GPAT genes, two types of genes have been cloned: microsomal (membrane-bound) and mitochondrial (membrane-bound) GPAT genes (Non-patent Document 2). Likewise, as plant GPAT genes, three types of genes have been cloned: microsomal (membrane-bound), mitochondrial (membrane-bound) and chloroplast (free) GPAT genes (Non-patent Document 3). In addition, as GPAT genes derived from the fungus *Saccharomyces cerevisiae*, two types of genes have been cloned: microsomal (membrane-bound) GPT2 (GAT1) and SCT1 (GAT2) genes (Non-patent Document 4). For these fungal genes, it has been shown that GPT2 has the ability to use a wide range of fatty acids covering from palmitic acid (16:0) to oleic acid (18:1) as a substrate, whereas SCT1 has a strong selectivity in using a $C_{16}$ fatty acid (e.g., palmitic acid (16:0), palmitoleic acid (16:1)) as a substrate (Non-patent Document 4). Moreover, GPAT genes have also been cloned from many other organisms.

Reports are also issued for GPATs derived from microorganisms of the genus *Mortierella*, which are lipid-producing fungi. With respect to GPAT derived from *Mortierella ramanniana*, microsomal GPAT has been isolated and found to use oleic acid (18:1) as an acyl donor with 5.4-fold selectivity compared to palmitic acid (16:0) (Non-patent Document 5). With respect to GPAT derived from *Mortierella alpina* (hereinafter also referred to as "*M. alpina*"), the microsomal fraction of this fungus has been reported to have glycerol-3-phosphate acyltransferase activity (Non-patent Document 6). In addition, when reacted in vitro with various acyl-CoAs, GPAT present in microsomes of *M. alpina* (which is in a membrane-bound state) has been found to use a wide range of PUFAs including oleic acid (18:1), linolic acid (18:2), dihomo-γ-linolenic acid (DGLA) (20:3) and arachidonic acid (20:4) as a substrate while retaining high activity (Patent Document 1). Moreover, when expressed in *Yarrowia lipolytica* transformed to allow biosynthesis of up to eicosapentaenoic acid (EPA), GPAT cloned from *M. alpina* (ATCC #16266) has been found to provide a higher ratio of dihomo-γ-linolenic acid (DGLA) (20:3) and a lower ratio of oleic acid (18:1) among all fatty acids. This result indicates that PUFA with a longer chain length and a higher unsaturation degree is more selectively incorporated (Patent Document 2).

Patent Document 1: International Publication No. WO2004/087902
Patent Document 2: US Patent Publication No. 2006/0094091
Non-patent Document 1: Lipids, 39, 1147 (2004)
Non-patent Document 2: Biochimica et Biophysica Acta, 1348, 17-26, 1997
Non-patent Document 3: Biochimica et Biophysica Acta, 1348, 10-16, 1997
Non-patent Document 4: The Journal of Biological Chemistry, 276 (45), 41710-41716, 2001
Non-patent Document 5: The Biochemical Journal, 355, 315-322, 2001
Non-patent Document 6: Biochemical Society Transactions, 28, 707-709, 2000

DISCLOSURE OF THE INVENTION

Problems to be Solved by the Invention

However, even if GPAT genes previously reported are introduced into and expressed in host cells, fatty acid compositions produced by the hosts are limited due to the substrate specificity of the expressed enzymes. For this reason, there is a need to identify a novel gene which allows production of a fatty acid composition whose fatty acid rate differs from that previously reported.

Means for Solving the Problems

The object of the present invention is to provide a protein or nucleic acid which allows production of fats and oils with a desired fatty acid rate and/or enrichment of desired fatty acids by being expressed in or introduced into host cells.

To achieve the above object, the inventors of the present invention have made extensive and intensive efforts. First, EST analysis was performed on a lipid-producing fungus, *Mortierella alpina*, to extract sequences sharing high identity with known GPAT genes. To obtain the entire open reading frame (ORF) encoding GPAT, genes were further cloned by cDNA library screening or PCR. As a result of attempting to introduce these genes into highly proliferative host cells (e.g., yeast cells) to thereby produce a desired fatty acid composition, the inventors succeeded in cloning a gene related to a novel GPAT with different substrate specificity, which allows production of a fatty acid composition different from those produced by hosts expressing conventional GPATs. This led to the completion of the present invention. Namely, the present invention is as follows.

(1) A nucleic acid comprising a nucleotide sequence shown in any one of (a) to (e) below:

(a) a nucleotide sequence which encodes a protein consisting of an amino acid sequence with deletion, substitution or addition of one or more amino acids in the amino acid sequence shown in SEQ ID NO: 2 and having glycerol-3-phosphate acyltransferase activity;

(b) a nucleotide sequence which is hybridizable under stringent conditions with a nucleic acid consisting of a nucleotide sequence complementary to a nucleotide sequence consisting of SEQ ID NO: 4 and which encodes a protein having glycerol-3-phosphate acyltransferase activity;

(c) a nucleotide sequence which consists of a nucleotide sequence sharing an identity of 70% or more with a nucleotide sequence consisting of SEQ ID NO: 4 and which encodes a protein having glycerol-3-phosphate acyltransferase activity;

(d) a nucleotide sequence which encodes an amino acid sequence sharing an identity of 70% or more with an amino acid sequence consisting of SEQ ID NO: 2 and which encodes a protein having glycerol-3-phosphate acyltransferase activity; or (e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 and which encodes a protein having glycerol-3-phosphate acyltransferase activity.

(2) The nucleic acid according to (1) above, which comprises a nucleotide sequence shown in any one of (a) to (c) below:

(a) a nucleotide sequence which encodes a protein consisting of an amino acid sequence with deletion, substitution or addition of 1 to 10 amino acids in the amino acid sequence shown in SEQ ID NO: 2 and having glycerol-3-phosphate acyltransferase activity;

(b) a nucleotide sequence which is hybridizable under conditions of 2×SSC at 50° C. with a nucleic acid consisting of a nucleotide sequence complementary to a nucleotide sequence consisting of SEQ ID NO: 4 and which encodes a protein having glycerol-3-phosphate acyltransferase activity; or (c) a nucleotide sequence which encodes an amino acid sequence sharing an identity of 90% or more with an amino acid sequence consisting of SEQ ID NO: 2 and which encodes a protein having glycerol-3-phosphate acyltransferase activity.

(3) A nucleic acid comprising a nucleotide sequence shown in any one of (a) to (c) below or a fragment thereof:

(a) the nucleotide sequence shown in SEQ ID NO: 4;

(b) a nucleotide sequence encoding a protein consisting of the amino acid sequence shown in SEQ ID NO: 2; or (c) the nucleotide sequence shown in SEQ ID NO: 1.

(4) A nucleic acid comprising a nucleotide sequence shown in any one of (a) to (e) below:

(a) a nucleotide sequence which encodes the following protein:

a protein which consists of an amino acid sequence with deletion, substitution or addition of one or more amino acids in the amino acid sequence shown in SEQ ID NO: 2 and which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content;

(b) a nucleotide sequence which is hybridizable under stringent conditions with a nucleic acid consisting of a nucleotide sequence complementary to a nucleotide sequence consisting of SEQ ID NO: 4 and which encodes the following protein:

a protein which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content;

(c) a nucleotide sequence which consists of a nucleotide sequence sharing an identity of 70% or more with a nucleotide sequence consisting of SEQ ID NO: 4 and which encodes the following protein:

a protein which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content;

(d) a nucleotide sequence which encodes the following protein:

a protein which consists of an amino acid sequence sharing an identity of 70% or more with an amino acid sequence consisting of SEQ ID NO: 2 and which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content; or (e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 and which encodes the following protein:

a protein which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content.

(5) The nucleic acid according to (4) above, which comprises a nucleotide sequence shown in any one of (a) to (c) below:

(a) a nucleotide sequence which encodes the following protein:

a protein which consists of an amino acid sequence with deletion, substitution or addition of 1 to 10 amino acids in the amino acid sequence shown in SEQ ID NO: 2 and which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content; iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content;

(b) a nucleotide sequence which is hybridizable under conditions of 2×SSC at 50° C. with a nucleic acid consisting of a nucleotide sequence complementary to a nucleotide sequence consisting of SEQ ID NO: 4 and which encodes the following protein:

a protein which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content; or (c) a nucleotide sequence which encodes the following protein:

a protein which consists of an amino acid sequence sharing an identity of 90% or more with an amino acid sequence consisting of SEQ ID NO: 2 and which has the ability to yield a fatty acid rate ensuring a higher ratio of at least one or more of i) to v) shown below in the fatty acid rate of a host expressing the protein than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content.

(6) A protein shown in (a) or (b) below:
(a) a protein which consists of an amino acid sequence with deletion, substitution or addition of one or more amino acids in SEQ ID NO: 2 and which has glycerol-3-phosphate acyltransferase activity; or
(b) a protein which consists of an amino acid sequence sharing an identity of 70% or more with an amino acid sequence consisting of SEQ ID NO: 2 and which has glycerol-3-phosphate acyltransferase activity.

(7) A protein shown in (a) or (b) below:
(a) a protein which consists of an amino acid sequence with deletion, substitution or addition of one or more amino acids in SEQ ID NO: 2 and which has the ability to yield a fatty acid rate ensuring a higher ratio of at least one or more of i) to v) shown below in the fatty acid rate of a host expressing a protein consisting of the amino acid sequence than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content; or (b) a protein which consists of an amino acid sequence sharing an identity of 70% or more with an amino acid sequence consisting of SEQ ID NO: 2 and which has the ability to yield a fatty acid rate ensuring a higher ratio of at least one or more of i) to v) shown below in the fatty acid rate of a host expressing a protein consisting of the amino acid sequence than in the fatty acid rate of a host not expressing the protein:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content.

(8) A protein consisting of the amino acid sequence shown in SEQ ID NO: 2.

(9) A recombinant vector comprising the nucleic acid according to any one of (1) to (5) above.

(10) A transformant transformed with the recombinant vector according to (9) above.

(11) A fatty acid composition obtained by culturing the transformant according to (10) above, wherein at least one or more of i) to v) shown below is higher in the fatty acid rate of the fatty acid composition than in a cultured product obtained by culturing a host which is not transformed with the recombinant vector according to (9) above:

i) the oleic acid content;
ii) the ratio of the oleic acid content to the palmitic acid content;
iii) the ratio of the total content of stearic acid and oleic acid to the palmitic acid content;

iv) the ratio of the $C_{18}$ fatty acid content to the $C_{16}$ fatty acid content; and v) the ratio of the arachidonic acid and/or dihomo-γ-linolenic acid content.

(12) A method for preparing a fatty acid composition, which comprises collecting the fatty acid composition according to (11) above from a cultured product obtained by culturing the transformant according to (10) above.

(13) A food product comprising the fatty acid composition according to (11) above.

Advantages of the Invention

The GPAT of the present invention has substrate specificity different from that of conventional GPATs, and allows a host to produce a fatty acid composition whose fatty acid rate differs from that of fatty acid compositions produced by hosts expressing conventional GPATs. As a result, the GPAT of the present invention enables the provision of lipids having desired properties and effects, and is useful as being applicable to foods, cosmetics, pharmaceuticals, soaps, etc.

Moreover, the GPAT of the present invention allows improvement in the ability to produce fatty acids and storage lipids, and hence is preferred as a means for improving the productivity of polyunsaturated fatty acids in microorganisms and plants.

BRIEF DESCRIPTION OF THE DRAWINGS

FIG. 1 shows the cDNA sequence (SEQ ID NO: 1) of GPAT2 according to the present invention, along with its deduced amino acid sequence (SEQ ID NO: 2). In the FIGURE, "*" represents an amino acid residue which appears to be important for GPAT activity, and "+" represents an amino acid residue which appears to be important for binding to glycerol-3-phosphate.

BEST MODE FOR CARRYING OUT THE INVENTION

The present invention relates to novel genes for glycerol-3-phosphate acyltransferase derived from the genus *Mortierella*, characterized by acylating glycerol-3-phosphate to generate lysophosphatidic acid.

Glycerol-3-phosphate acyltransferase (GPAT) in the present invention is an enzyme that catalyzes a reaction in which glycerol-3-phosphate is acylated to generate lysophosphatidic acid. An acyl donor is generally acylCoA, but is not limited thereto. An acyl acceptor in the acyl transfer reaction catalyzed by the protein of the present invention is glycerol-3-phosphate, but is not limited thereto.

Nucleic Acids of the Present Invention Encoding glycerol-3-phosphate acyltransferase Glycerol-3-phosphate acyltransferase (GPAT) in the present invention encompasses GPAT2. The correspondence between cDNA, CDS, ORF and amino acid sequences of a nucleic acid encoding GPAT2 is summarized in Table 1 below.

TABLE 1

| | GPAT2 | |
|---|---|---|
| | SEQ ID NO: | Corresponding region in SEQ ID NO: 1 |
| cDNA | SEQ ID NO: 1 | ***** |
| CDS | SEQ ID NO: 3 | Positions 113-1891 |

TABLE 1-continued

| | GPAT2 | |
|---|---|---|
| | SEQ ID NO: | Corresponding region in SEQ ID NO: 1 |
| ORF | SEQ ID NO: 4 | Positions 113-1888 |
| Amino acid sequence | SEQ ID NO: 2 | ***** |

Namely, sequences related to GPAT2 of the present invention include SEQ ID NO: 2 (amino acid sequence of GPAT2), SEQ ID NO: 4 (sequence representing the ORF region of GPAT2), SEQ ID NO: 3 (sequence representing the CDS region of GPAT2) and SEQ ID NO: 1 (nucleotide sequence of cDNA for GPAT2). Among them, SEQ ID NO: 3 corresponds to nucleotides 113-1891 of SEQ ID NO: 1, while SEQ ID NO: 4 corresponds to nucleotides 113-1888 of SEQ ID NO: 1 or nucleotides 1-1776 of SEQ ID NO: 3.

The nucleic acids of the present invention encompass single-stranded and double-stranded DNAs as well as complementary RNAs thereof, which may be either naturally occurring or artificially prepared. DNAs include, but are not limited to, genomic DNAs, cDNAs corresponding to the genomic DNAs, chemically synthesized DNAs, PCR-amplified DNAs, as well as combinations thereof and DNA/RNA hybrids.

Preferred embodiments for the nucleic acids of the present invention include (a) the nucleotide sequence shown in SEQ ID NO: 4, (b) a nucleotide sequence encoding a protein consisting of the amino acid sequence shown in SEQ ID NO: 2, and (c) the nucleotide sequence shown in SEQ ID NO: 1.

The above nucleotide sequence shown in SEQ ID NO: 4, nucleotide sequence encoding a protein consisting of the amino acid sequence shown in SEQ ID NO: 2, and nucleotide sequence shown in SEQ ID NO: 1 are as shown in Table 1.

To obtain these nucleotide sequences, nucleotide sequence data of ESTs or genomic DNAs from organisms having GPAT activity may be used to search a nucleotide sequence encoding a protein sharing high identity with known proteins having GPAT activity. Preferred organisms having GPAT activity are lipid-producing fungi including, but not limited to, *M. alpina*.

For EST analysis, a cDNA library is first prepared. As to techniques for cDNA library preparation, reference may be made to "Molecular Cloning, A Laboratory Manual 3rd ed." (Cold Spring Harbor Press (2001)). Alternatively, a commercially available cDNA library preparation kit may be used. Techniques for cDNA library preparation suitable for the present invention are as follows, by way of example. Namely, an appropriate strain of *M. alpina*, a lipid-producing fungus, is inoculated into an appropriate medium and pre-cultured for an appropriate period. Culture conditions suitable for this pre-culture include, for example, medium composition of 1.8% glucose, 1% yeast extract and pH 6.0, a culture period of 3 days, and a culture temperature of 28° C. The pre-cultured product is then subjected to main culture under appropriate conditions. Medium composition suitable for main culture may be, for example, 1.8% glucose, 1% soybean powder, 0.1% olive oil, 0.01% Adekanol, 0.3% $KH_2PO_4$, 0.1% $Na_2SO_4$, 0.05% $CaCl_2 \cdot 2H_2O$, 0.05% $MgCl_2 \cdot 6H_2O$ and pH 6.0. Culture conditions suitable for main culture may be, for example, aerobic spinner culture at 300 rpm, 1 vvm, 26° C. for 8 days. An appropriate amount of glucose may be added during culture. The cultured product is sampled at appropriate time points during main culture, from which the cells are then collected to prepare total RNA. For preparation of total RNA, it is possible to use any known technique, such as guanidine hydrochloride/CsCl method. The resulting total RNA may be treated with a commercially available kit to purify poly(A)$^+$ RNA. Further, a cDNA library may be prepared with a commercially available kit. Then, any clone from the cDNA library thus prepared is determined for its nucleotide sequence by using primers which are designed on a vector to allow determination of the nucleotide sequence of an insert. As a result, ESTs can be obtained. For example, when a ZAP-cDNA GigapackIII Gold Cloning Kit (STRATAGENE) is used for cDNA library preparation, directional cloning can be performed.

When compared for their ORF nucleotide sequences, the GPAT2 gene of the present invention and a known GPAT1 gene derived from *M. alpina* (ATCC #16266) share 42.0% identity. It should be noted that when analyzed by BLASTX, the GPAT2 gene of the present invention shares 36.9% identity with a nucleotide sequence encoding an *Aspergillus nidulans*-derived 1-acyl-sn-glycerol-3-phosphate acyltransferase-like putative protein sequence (GB Accession No. EAA62242) having the lowest E-value (i.e., showing the highest identity) and shares 36.6% identity with a nucleotide sequence encoding *Saccharomyces cerevisiae*-derived glycerol-3-phosphate acyltransferase Sct1p (GB Accession No. CAC85390) showing the highest identity among proteins whose functions have been clarified.

Likewise, the amino acid sequence identity between GPAT2 of the present invention and known GPAT1 derived from *M. alpina* (ATCC #16266) is 15.7%. It should be noted that when analyzed by BLASTX, the GPAT2 gene of the present invention shares 17.0% identity with an *Aspergillus nidulans*-derived 1-acyl-sn-glycerol-3-phosphate acyltransferase-like putative protein sequence (GB Accession No. EAA62242) having the lowest E-value (i.e., showing the highest identity) and shares 15.0% identity with *Saccharomyces cerevisiae*-derived glycerol-3-phosphate acyltransferase Sct1p (GB Accession No. CAC85390) showing the highest identity among proteins whose functions have been clarified.

The present invention also encompasses nucleic acids functionally equivalent to a nucleic acid comprising the above nucleotide sequence shown in SEQ ID NO: 4 (hereinafter also referred to as "the nucleotide sequence of the present invention") or nucleotide sequence encoding a protein consisting of the amino acid sequence shown in SEQ ID NO: 2 (hereinafter also referred to as "the amino acid sequence of the present invention"). The phrase "functionally equivalent" is intended to mean that a protein encoded by the nucleotide sequence of the present invention or a protein consisting of the amino acid sequence of the present invention has GPAT activity. In addition to this GPAT activity, a protein encoded by the nucleotide sequence of the present invention or a protein consisting of the amino acid sequence of the present invention may have the ability to yield a fatty acid rate ensuring a higher ratio of at least one or more of:

i) the oleic acid content;
ii) the ratio of the oleic acid content to the palmitic acid content;
iii) the ratio of the total content of stearic acid and oleic acid to the palmitic acid content;
iv) the ratio of the $C_{18}$ fatty acid content to the $C_{16}$ fatty acid content; and
v) the ratio of the arachidonic acid and/or dihomo-γ-linolenic acid content in the fatty acid rate of a host expressing the protein than in the fatty acid rate of a host not expressing the protein (such a protein is hereinafter also referred to as a "protein having the ability to yield the fatty acid rate of GPAT in the present invention").

A specific example is a nucleic acid comprising a nucleotide sequence encoding a protein having the ability to yield a fatty acid rate satisfying at least one or more of the following:

i) the oleic acid content is 47% or more, preferably 48% or more, 49% or more, 50% or more, 51% or more;
ii) the ratio of the oleic acid content to the palmitic acid content is 8.0 or more, preferably 9.0 or more, 10.0 or more, 10.5 or more;
iii) the ratio of the total content of stearic acid and oleic acid to the palmitic acid content is 8.5 or more, preferably 9.0 or more, 10.0 or more, 11.0 or more, 11.5 or more;
iv) the ratio of the $C_{18}$ fatty acid content to the $C_{16}$ fatty acid content is 1.2 or more, preferably 1.3 or more, 1.4 or more; and
v) the arachidonic acid content is 0.47 or more, preferably 0.50 or more, 0.55 or more, 0.60 or more, and/or the dihomo-γ-linolenic acid content is 0.34 or more, preferably 0.40 or more, 0.50 or more, 0.55 or more, when the above nucleotide sequence of the present invention is inserted into expression vector pYE22m (Biosci. Biotech. Biochem., 59, 1221-1228, 1995) and transformed into a yeast host, *Saccharomyces cerevisiae* strain EH13-15 (Appl. Microbiol. Biotechnol., 30, 515-520, 1989), and the resulting transformant is cultured to collect the cells, which are then analyzed for fatty acids by the procedures described in Example 6 below. More preferred is a nucleic acid comprising a nucleotide sequence encoding a protein having both GPAT activity and the above ability to yield the fatty acid rate of GPAT in the present invention.

One of the characteristic features in the fatty acid composition of the present invention is high arachidonic acid content. Arachidonic acid, a substance represented by the chemical formula $C_{20}H_{32}O_2$ and having a molecular weight of 304.47, is a carboxylic acid containing 20 carbon atoms and 4 double bonds ([20:4(n–6)]) and classified as a member of the (n–6) series. Arachidonic acid is present as an important phospholipid (particularly phosphatidylethanolamine, phosphatidylcholine, phosphatidylinositol) in animal cell membranes and is contained in abundance in the brain. Moreover, arachidonic acid serves as a starting material for a series of eicosanoids (e.g., prostaglandin, thromboxane, leukotriene) generated by the arachidonic acid cascade, and is also important as a second messenger in intercellular signaling. On the other hand, arachidonic acid is synthesized from linolic acid in the animal body. However, depending on their species or age, some animals do not exert this function sufficiently to produce the required amount of arachidonic acid or have no function to produce arachidonic acid. Thus, arachidonic acid should be taken from food sources and can be regarded as an essential fatty acid.

The arachidonic acid content in the fatty acid composition of the present invention may be measured as follows, by way of example. Namely, a plasmid for GPAT2 of the present invention is inserted into a vector such as pDuraSC or pDura5MCS, as described in Example 8, and transformed into a *M. alpina* strain. The resulting transformant is allowed to express and cultured according to the procedures described in Example 8. The cultured cells thus obtained are used to measure the fatty acid content in the cells and/or the arachidonic acid content per medium, etc. To analyze the arachidonic acid content, etc., for example, fatty acids in the resulting cultured cells are derived into corresponding fatty acid methyl esters by the hydrochloric acid/methanol method, and then extracted with hexane. After distilling off hexane, the fatty acids are analyzed by gas chromatography. According to this analysis, *M. alpina* transformed with GPAT2 of the present invention has been found to show not only high fatty acid content in the cells, but also high arachidonic acid production per medium. Thus, the fatty acid composition of the present invention having high arachidonic acid content is preferred because it enables the efficient intake of arachidonic acid.

Another characteristic feature in the fatty acid composition of the present invention is high dihomo-γ-linolenic acid content. Dihomo-γ-linolenic acid (DGLA), a substance represented by the chemical formula $C_{20}H_{34}O_2$ and having a molecular weight of 306.48, is a carboxylic acid containing 20 carbon atoms and 3 double bonds ([20:3(n–6)]) and classified as a member of the (n–6) series. DGLA is obtained by elongation of γ-linolenic acid (18:3(n–6)). Upon addition of one more double bond to DGLA, arachidonic acid is generated.

Such nucleic acids that are functionally equivalent to the nucleic acids of the present invention include a nucleic acid comprising a nucleotide sequence shown in any one of (a) to (e) below. It should be noted that when used to describe the nucleotide sequences listed below, the phrase "the above activity of the present invention" is intended to mean "GPAT activity and/or the ability to yield the fatty acid rate of GPAT in the present invention" defined above.

(a) A nucleotide sequence which encodes a protein consisting of an amino acid sequence with deletion, substitution or addition of one or more amino acids in the amino acid sequence shown in SEQ ID NO: 2 and having the above activity of the present invention.

Nucleotide sequences contained in the nucleic acids of the present invention include a nucleotide sequence which encodes a protein consisting of an amino acid sequence with deletion, substitution or addition of one or more amino acids in the amino acid sequence shown in SEQ ID NO: 2 and having the above activity of the present invention.

More specifically, it is a nucleotide sequence which encodes a protein consisting of:

(i) an amino acid sequence with deletion of one or more (preferably one or several (e.g., 1-180, 1-150, 1-100, 1-50, 1-30, 1-25, 1-20, 1-15, 1-10, more preferably 1-5)) amino acids in the amino acid sequence shown in SEQ ID NO: 2;

(ii) an amino acid sequence with substitution of other amino acids for one or more (preferably one or several (e.g., 1-180, 1-150, 1-100, 1-50, 1-30, 1-25, 1-20, 1-15, 1-10, more preferably 1-5)) amino acids in the amino acid sequence shown in SEQ ID NO: 2;

(iii) an amino acid sequence with addition of other one or more (preferably one or several (e.g., 1-180, 1-150, 1-100, 1-50, 1-30, 1-25, 1-20, 1-15, 1-10, more preferably 1-5)) amino acids in the amino acid sequence shown in SEQ ID NO: 2; or (iv) an amino acid sequence with any combination of (i) to (iii) above, and having the above activity of the present invention.

Among the above modifications, substitution is preferably conservative, which means the replacement of a certain amino acid residue by another residue having similar physical and chemical characteristics. It may be any substitution as long as it does not substantially alter the structural characteristics of the original sequence. For example, any substitution is possible as long as the substituted amino acids do not disrupt a helix present in the original sequence or do not disrupt any other type of secondary structure characterizing the original sequence.

Conservative substitution is generally introduced by synthesis in biological systems or chemical peptide synthesis, preferably by chemical peptide synthesis. In this case, substituents may include unnatural amino acid residues, as well as peptidomimetics, and reversed or inverted forms of amino acid sequences in which unsubstituted regions are reversed or inverted.

Amino acid residues are classified and listed below in groups of mutually substitutable members, but are not limited to the following:

Group A: leucine, isoleucine, norleucine, valine, norvaline, alanine, 2-aminobutanoic acid, methionine, O-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and

Group G: phenylalanine and tyrosine.

Non-conservative substitution may involve the exchange of a member of one of the above classes for a member from another class. In this case, for the purpose of maintaining biological functions of the proteins of the present invention, it is preferable to consider the hydropathic index of amino acids (hydropathic amino acid index) (Kyte et al., J. Mol. Biol., 157:105-131 (1982)).

In the case of non-conservative substitution, amino acid substitutions may also be accomplished on the basis of hydrophilicity.

In the specification and drawings of the present application, nucleotides, amino acids and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomer, unless otherwise specified.

Stereoisomers (e.g., D-amino acids) of the above amino acids, unnatural amino acids such as α,α-disubstituted amino acids, N-alkylamino acids, lactic acid, and other unconventional amino acids may also be members constituting the proteins of the present invention.

It should be noted that in the protein notation used herein, the lefthand direction is the amino terminal direction and the righthand direction is the carboxy terminal direction, in accordance with standard usage and convention.

Similarly, unless otherwise specified, the lefthand end of single-stranded polynucleotide sequences is the 5'-end and the lefthand direction of double-stranded polynucleotide sequences is referred to as the 5' direction.

Those skilled in the art would be able to design and prepare appropriate mutants of the proteins described herein by using techniques known in the art. For example, when targeting a region which appears to be less important for the biological activity of the protein of the present invention, it is possible to identify a suitable region in the protein molecule whose structure can be changed without impairing the biological activity of the protein of the present invention. It is also possible to identify residues or regions in the molecule, which are conserved between similar proteins. Moreover, it is also possible to introduce conservative amino acid substitutions into a region which appears to be important for the biological activity or structure of the protein of the present invention, without impairing the biological activity and without adversely affecting the polypeptide structure of the protein. Particularly in the present invention, as double underlined in FIG. 1, the amino acid sequence of the GPAT of the present invention contains, at residues 87-93, a motif which is similar to the consensus motif "HXXXXD (HX$_4$D)" (J. Bacteriology, 180, 1425-1430, 1998) essential for glycerolipid acyltransferase (conserved histidine and aspartic acid residues are indicated with *). In the above consensus motif, X represents any amino acid residue. This motif would also be important for the GPAT of the present invention to retain GPAT activity. Likewise, residues 87, 93 and 172 in the amino acid sequence of the GPAT of the present invention, which are indicated with * in FIG. 1, would be important for the activity of the GPAT of the present invention. Moreover, residues 138 and 174 would be important for binding between the GPAT of the present invention and glycerol-3-phosphate. Thus, mutants according to the present invention are not limited in any way as long as the above consensus motif and the above residues are conserved.

Those skilled in the art would be able to conduct a so-called structure-function study which identifies residues, in the protein of the present invention and in a similar peptide thereof, that are important for biological activity or structure, and compares amino acid residues between these two peptides, thereby predicting which residues in the protein similar to the protein of the present invention are amino acid residues corresponding to those important for biological activity or structure. Moreover, chemically similar amino acid substitutions may be chosen for the amino acid residues thus predicted to thereby select a mutant which retains the biological activity of the protein of the present invention. Likewise, those skilled in the art would also be able to analyze the three-dimensional structure and amino acid sequence of this protein mutant. The analysis results thus obtained can further be used to predict the alignment of amino acid residues with respect to the three-dimensional structure of the protein. Since amino acid residues predicted to be on the protein surface may be involved in important interactions with other molecules, those skilled in the art would be able to prepare a mutant which causes no change in these amino acid residues predicted to be on the protein surface, on the basis of analysis results as mentioned above. Moreover, those skilled in the art would also be able to prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention when a comparison is made with the following case where a mutant having substitution of a specific amino acid residue shows lower biological activity than that of the protein of the present invention, where such a mutant shows no biological activity, or where such a mutant produces unsuitable activity to inhibit the biological activity of the protein of the present invention. Moreover, based on information collected from such routine experiments, those skilled in the art may readily analyze amino acid substitutions undesirable for mutants of the protein of the present invention either alone or in combination with other mutations.

As described above, a protein consisting of an amino acid sequence with deletion, substitution or addition of one or more amino acids in the amino acid sequence shown in SEQ ID NO: 2 can be prepared according to techniques such as site-directed mutagenesis as described in "Molecular Cloning, A Laboratory Manual 3rd ed." (Cold Spring Harbor Press (2001)), "Current Protocols in Molecular Biology" (John Wiley & Sons (1987-1997), Kunkel (1985) Proc. Natl. Acad. Sci. USA 82: 488-92, and Kunkel (1988) Method. Enzymol. 85: 2763-6. Preparation of a mutant with such a mutation including amino acid deletion, substitution or addition may be accomplished, for example, by known procedures such as Kunkel method or Gapped duplex method using a mutation-introducing kit based on site-directed mutagenesis such as a QuikChange™ Site-Directed Mutagenesis Kit (Stratagene), a GeneTailor™ Site-Directed Mutagenesis System (Invitrogen) or a TaKaRa Site-Directed Mutagenesis System (e.g., Mutan-K, Mutan-Super Express Km; Takara Bio Inc., Japan).

Techniques for allowing deletion, substitution or addition of one or more amino acids in the amino acid sequences of proteins while retaining their activity include site-directed mutagenesis mentioned above, as well as other techniques such as those for treating a gene with a mutagen, and those in which a gene is selectively cleaved to remove, substitute or add a selected nucleotide or nucleotides, and then ligated.

A preferred nucleotide sequence contained in the nucleic acids of the present invention is a nucleotide sequence which encodes a protein consisting of an amino acid sequence with deletion, substitution or addition of 1 to 10 amino acids in the amino acid sequence shown in SEQ ID NO: 2 and having GPAT activity.

Moreover, nucleotide sequences contained in the nucleic acids of the present invention also include a nucleotide sequence which encodes a protein consisting of an amino acid sequence with deletion, substitution or addition of 1 to 10 amino acids in SEQ ID NO: 2 and having the above activity of the present invention.

There is no limitation on the number or sites of amino acid mutations or modifications in the protein of the present invention, as long as the resulting mutant retains GPAT activity or the ability to yield the fatty acid rate of GPAT in the present invention.

GPAT activity in the present invention or the ability to yield the fatty acid rate of GPAT in the present invention can be measured in a known manner. For example, reference may be made to the following document: Biochem. J., 355, 315-322, 2001.

"GPAT activity" in the present invention may be measured as follows, by way of example. A microsomal fraction is prepared from yeast cells transformed to express the GPAT of the present invention, as described in, e.g., J. Bacteriology, 173, 2026-2034 (1991). To a reaction solution containing 0.44 mM glycerol-3-phosphate, 0.36 mM acyl-CoA, 0.5 mM DTT, 1 mg/ml BSA and 2 mM MgCl$_2$ in 50 mM Tris-HCl (pH 7.5), the above microsomal fraction is then added and reacted at 28° C. for an appropriate period. Chloroform:methanol is added to stop the reaction, followed by lipid extraction. The resulting lipids are fractionated by thin-layer chromatography or other techniques, whereby the amount of lysophosphatidic acid generated can be quantified.

Likewise, "the ability to yield the fatty acid rate of GPAT" in the present invention may be measured as follows, by way of example. To lyophilized cells obtained by the method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography.

(b) A nucleotide sequence which is hybridizable under stringent conditions with a nucleic acid consisting of a nucleotide sequence complementary to a nucleotide sequence consisting of SEQ ID NO: 4 and which encodes a protein having the above activity of the present invention.

Nucleotide sequences contained in the nucleic acids of the present invention include a nucleotide sequence which is hybridizable under stringent conditions with a nucleic acid consisting of a nucleotide sequence complementary to a nucleotide sequence consisting of SEQ ID NO: 4 and which encodes a protein having the above activity of the present invention. SEQ ID NO: 4 and GPAT activity are as described above.

To obtain the above nucleotide sequence, a probe may be prepared from an appropriate fragment in a manner known to those skilled in the art, and this probe may be used in known hybridization techniques such as colony hybridization, plaque hybridization or Southern blotting to obtain the nucleotide sequence from a cDNA library, a genomic library or the like.

As to detailed procedures for hybridization techniques, reference may be made to "Molecular Cloning, A Laboratory Manual 3rd ed." (Cold Spring Harbor Press (2001); particularly Sections 6-7), "Current Protocols in Molecular Biology" (John Wiley & Sons (1987-1997); particularly Sections 6.3-6.4), "DNA Cloning 1: Core Techniques, A Practical Approach 2nd ed." (Oxford University (1995); particularly Section 2.10 for hybridization conditions).

The strength of hybridization is determined primarily by hybridization conditions, more preferably by hybridization conditions and washing conditions. The term "stringent conditions" as used herein is intended to include moderately or highly stringent conditions.

More specifically, moderately stringent conditions include, for example, hybridization conditions of 1×SSC to 6×SSC at 42° C. to 55° C., more preferably 1×SSC to 3×SSC at 45° C. to 50° C., and most preferably 2×SSC at 50° C. In certain cases such as where a hybridization solution contains about 50% formamide, a temperature which is 5° C. to 15° C. lower than the above temperature is used. Washing conditions may be 0.5×SSC to 6×SSC at 40° C. to 60° C. During hybridization and washing, 0.05% to 0.2% SDS, preferably about 0.1% SDS may usually be added.

Highly stringent (high stringent) conditions include hybridization and/or washing at higher temperature and/or lower salt concentration, compared to the moderately stringent conditions. For example, hybridization conditions may be 0.1×SSC to 2×SSC at 55° C. to 65° C., more preferably 0.1×SSC to 1×SSC at 60° C. to 65° C., and most preferably 0.2×SSC at 63° C. Washing conditions may be 0.2×SSC to 2×SSC at 50° C. to 68° C., and more preferably 0.2×SSC at 60° C. to 65° C.

Hybridization conditions particularly used in the present invention include, but are not limited to, prehybridization in 5×SSC, 1% SDS, 50 mM Tris-HCl (pH 7.5) and 50% formamide at 42° C., overnight incubation at 42° C. in the presence of a probe to form hybrids, and the subsequent three washings in 0.2×SSC, 0.1% SDS at 65° C. for 20 minutes.

It is also possible to use a commercially available hybridization kit which uses no radioactive substance as a probe. Specific examples include hybridization with a DIG nucleic acid detection kit (Roche Diagnostics) or with an ECL direct labeling & detection system (Amersham).

A preferred nucleotide sequence falling within the present invention is a nucleotide sequence which is hybridizable under conditions of 2×SSC at 50° C. with a nucleic acid consisting of a nucleotide sequence complementary to a nucleotide sequence consisting of SEQ ID NO: 4 and which encodes a protein having GPAT activity.

(c) A nucleotide sequence which consists of a nucleotide sequence sharing an identity of 70% or more with a nucleotide sequence consisting of SEQ ID NO: 4 and which encodes a protein having the above activity of the present invention.

Nucleotide sequences contained in the nucleic acids of the present invention include a nucleotide sequence which consists of a nucleotide sequence sharing an identity of at least 70% or more with the nucleic acid sequence shown in SEQ ID NO: 4 and which encodes a protein having the above activity of the present invention.

Preferred examples include nucleic acids comprising a nucleotide sequence which shares an identity of at least 75%, more preferably 80% (e.g., 85% or more, even more preferably 90% or more, more particularly 95%, 98% or 99%) with the nucleic acid sequence shown in SEQ ID NO: 4 and which encodes a protein having the above activity of the present invention.

The percent identity between two nucleic acid sequences can be determined by visual inspection and mathematical calculation, or more preferably by using a computer program to compare sequence information between two nucleic acids. Computer programs for sequence comparison include, for example, the BLASTN program (Altschul et al. (1990) J. Mol. Biol. 215: 403-10) version 2.2.7, available for use via the National Library of Medicine website: http://www.ncbi.nlm.nih.gov/blast/bl2seq/bls.html, or the WU-BLAST 2.0 algorithm. Standard default parameter settings for WU-BLAST 2.0 are described at the following Internet site: http://blast.wustl.edu.

(d) A nucleotide sequence which encodes an amino acid sequence sharing an identity of 70% or more with an amino acid sequence consisting of SEQ ID NO: 2 and which encodes a protein having the above activity of the present invention.

Nucleotide sequences contained in the nucleic acids of the present invention include a nucleotide sequence which encodes an amino acid sequence sharing an identity of 70% or more with an amino acid sequence consisting of SEQ ID NO: 2 and which encodes a protein having the above activity of the present invention. Proteins encoded by the nucleic acids of the present invention may also be those sharing identity with the amino acid sequence of GPAT2, as long as they are functionally equivalent to proteins having the above activity of the present invention.

Specific examples include amino acid sequences sharing an identity of 75% or more, preferably 80% or more, more preferably 85%, even more preferably 90% (e.g., 95%, more particularly 98%) with the amino acid sequence shown in SEQ ID NO: 2.

A preferred nucleotide sequence contained in the nucleic acids of the present invention is a nucleotide sequence which encodes an amino acid sequence sharing an identity of 90% or more with an amino acid sequence consisting of SEQ ID NO: 2 and which encodes a protein having the above activity of the present invention. More preferred is a nucleotide sequence which encodes an amino acid sequence sharing an identity of 95% or more with an amino acid sequence consisting of SEQ ID NO: 2 and which encodes a protein having the above activity of the present invention.

The percent identity between two amino acid sequences may be determined by visual inspection and mathematical calculation. Alternatively, the percent identity may be determined by using a computer program. Examples of such a computer program include BLAST, FASTA (Altschul et al., J. Mol. Biol., 215:403-410 (1990)) and ClustalW. In particular, various conditions (parameters) for an identity search with the BLAST program are described by Altschul et al. (Nucl.

Acids. Res., 25, p. 3389-3402, 1997) and publicly available via the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver.7 (Genetyx Corporation, Japan), DINASIS Pro (Hitachisoft, Japan) or Vector NTI (Infomax) for determination of the percent identity.

Certain alignment schemes for aligning amino acid sequences may also result in matching of a specific short region of the sequences, and it is also possible to detect a region with very high sequence identity in such a small aligned region even when there is no significant relationship between the full-length sequences used. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported).

(e) A nucleotide sequence which is hybridizable under stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention.

Nucleotide sequences contained in the nucleic acids of the present invention include a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention.

Such a protein consisting of the amino acid sequence shown in SEQ ID NO: 2 and hybridization conditions are as described above. Nucleotide sequences contained in the nucleic acids of the present invention include a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention.

The nucleic acids of the present invention also include a nucleic acid which comprises a nucleotide sequence with deletion, substitution or addition of one or more nucleotides in a nucleotide sequence consisting of SEQ ID NO: 4 and encoding a protein having the above activity of the present invention. More specifically, it is also possible to use a nucleic acid which comprises a nucleotide sequence selected from:

(i) a nucleotide sequence with deletion of one or more (preferably one or several (e.g., 1-540, 1-500, 1-400, 1-300, 1-200, 1-150, 1-100, 1-50, 1-30, 1-25, 1-20, 1-15, 1-10, more preferably 1-5)) nucleotides in the nucleotide sequence shown in SEQ ID NO: 4;

(ii) a nucleotide sequence with substitution of other nucleotides for one or more (preferably one or several (e.g., 1-540, 1-500, 1-400, 1-300, 1-200, 1-150, 1-100, 1-50, 1-30, 1-25, 1-20, 1-15, 1-10, more preferably 1-5)) nucleotides in the nucleotide sequence shown in SEQ ID NO: 4;

(iii) a nucleotide sequence with addition of other one or more (preferably one or several (e.g., 1-540, 1-500, 1-400, 1-300, 1-200, 1-150, 1-100, 1-50, 1-30, 1-25, 1-20, 1-15, 1-10, more preferably 1-5)) nucleotides in the nucleotide sequence shown in SEQ ID NO: 4; or (iv) a nucleotide sequence with any combination of (i) to (iii) above, and encoding a protein having the above activity of the present invention.

Preferred embodiments for the nucleic acids of the present invention also include a nucleic acid comprising a nucleotide sequence shown in any one of (a) to (c) below or a fragment thereof:

(a) the nucleotide sequence shown in SEQ ID NO: 4;
(b) a nucleotide sequence encoding a protein consisting of the amino acid sequence shown in SEQ ID NO: 2; or
(c) the nucleotide sequence shown in SEQ ID NO: 1.

The above (a) nucleotide sequence shown in SEQ ID NO: 4, (b) nucleotide sequence encoding a protein consisting of the amino acid sequence shown in SEQ ID NO: 2, and (c) nucleotide sequence shown in SEQ ID NO: 1 are as shown in Table 1. Fragments of these sequences may be either naturally occurring or artificially prepared, including regions contained in the above nucleotide sequences, i.e., ORF, CDS, a biologically active region, a region used as a primer as described later, and a region which may serve as a probe.

Glycerol-3-phosphate acyltransferase Proteins of the Present Invention

The proteins of the present invention, which may be either naturally occurring or artificially prepared, include a protein consisting of the amino acid sequence shown in SEQ ID NO: 2 and proteins functionally equivalent to this protein. Such a protein consisting of the amino acid sequence shown in SEQ ID NO: 2 is as described above. "Proteins functionally equivalent" are intended to mean proteins having "the above activity of the present invention," as explained in the section "Nucleic acids of the present invention encoding glycerol-3-phosphate acyltransferase" described above.

In the present invention, proteins functionally equivalent to a protein consisting of the amino acid sequence shown in SEQ ID NO: 2 include a protein shown in (a) or (b) below:

(a) a protein which consists of an amino acid sequence with deletion, substitution or addition of one or more amino acids in SEQ ID NO: 2 and which has the above activity of the present invention; or (b) a protein which consists of an amino acid sequence sharing an identity of 70% or more with an amino acid sequence consisting of SEQ ID NO: 2 and which has the above activity of the present invention.

Among the above, the amino acid sequence with deletion, substitution or addition of one or more amino acids in SEQ ID NO: 2 or the amino acid sequence sharing an identity of 70% or more with an amino acid sequence consisting of SEQ ID NO: 2 is as explained in the section "Nucleic acids of the present invention encoding glycerol-3-phosphate acyltransferase" described above. The phrase "protein which has the above activity of the present invention" is intended to also include mutants of a protein encoded by a nucleic acid comprising the nucleotide sequence of SEQ ID NO: 4, or mutated proteins with various modifications such as substitution, deletion or addition of one or more amino acids in the amino acid sequence shown in SEQ ID NO: 2, as well as their modified proteins whose amino acid side chains or the like are modified, and their fusion proteins with other proteins, as long as these proteins have GPAT activity and/or the ability to yield the fatty acid rate of GPAT in the present invention.

The proteins of the present invention may also be artificially prepared by chemical synthesis techniques such as Fmoc method (fluorenylmethyloxycarbonyl method) and tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation (Japan) or other manufacturers may be used for chemical synthesis.

Cloning of GPAT Nucleic Acids

The GPAT nucleic acids of the present invention can be cloned, for example, by screening from a cDNA library using an appropriate probe. They can also be cloned by PCR amplification with appropriate primers and the subsequent ligation to an appropriate vector. The clones thus obtained may further be subcloned into another vector.

For example, it is possible to use commercially available plasmid vectors including pBlue-Script™ SK(+) (Stratagene), pGEM-T (Promega), pAmp (TM: Gibco-BRL), p-Direct (Clontech) and pCR2.1-TOPO (Invitrogen). In the case of using PCR amplification, primers may be any regions of the nucleotide sequence shown in, e.g., SEQ ID NO: 1. By way of example, it is possible to use the following primers from SEQ ID NO: 1:

```
E-1:
                                        (SEQ ID NO: 6)
5'-CTGACTACCAAAACCAGCTGGACTTC-3' as an upstream
primer;
and E-2:
                                        (SEQ ID NO: 7)
5'-GGCAATTTCATCCAAGTTGTCCTCC-3' as a downstream
primer.
```

Then, PCR is performed on cDNA prepared from *M. alpina* cells with the above primers and DNA polymerase or the like. Although this procedure can be readily accomplished by those skilled in the art according to, e.g., "Molecular Cloning, A Laboratory Manual 3rd ed." (Cold Spring Harbor Press (2001)), PCR conditions in the present invention may be set as follows, by way of example:

Denaturation temperature: 90-95° C.
Annealing temperature: 40-60° C.
Elongation temperature: 60-75° C.
Number of cycles: 10 or more cycles.

The resulting PCR products may be purified in a known manner, for example, by using a kit (e.g., GENECLEAN (Funakoshi Co., Ltd., Japan), QIAquick PCR purification Kits (QIAGEN), ExoSAP-IT (GE Healthcare Bio-Sciences)), a DEAE-cellulose filter or a dialysis tube. In the case of using an agarose gel, the PCR products are subjected to agarose gel electrophoresis and nucleic acid fragments are excised from the agarose gel, followed by purification with GENECLEAN (Funakoshi Co., Ltd., Japan) or QIAquick Gel extraction Kits (QIAGEN) or by the freeze-squeeze method, etc.

The cloned nucleic acids can be determined for their nucleotide sequences with a nucleic acid sequencer.

Vector Construction for GPAT Expression and Transformant Preparation

The present invention also provides a recombinant vector comprising a nucleic acid encoding GPAT2 of the present invention. The present invention further provides a transformant transformed with the above recombinant vector.

Such a recombinant vector and transformant can be obtained as follows. Namely, a plasmid carrying a nucleic acid encoding the GPAT of the present invention is digested with restriction enzymes. Examples of restriction enzymes available for use include, but are not limited to, EcoRI, KpnI, BamHI and SalI. This digestion may be followed by blunt ending with T4 polymerase. The digested nucleic acid fragment is purified by agarose gel electrophoresis. This nucleic acid fragment may be integrated into an expression vector in a known manner to obtain a vector for GPAT expression. This expression vector is introduced into a host to prepare a transformant, which is then provided for expression of a desired protein.

In this case, the types of expression vector and host are not limited in any way as long as they allow expression of a desired protein. Examples of a host include fungi, bacteria, plants, animals or cells thereof. Fungi include filamentous fungi such as lipid-producing *M. alpina*, and yeast strains such as *Saccharomyces cerevisiae*. Bacteria include *Escherichia coli* (*E. coli*) and *Bacillus subtilis*. Likewise, plants include oil plants such as rapeseed, soybean, cotton, safflower and flax.

As lipid-producing strains, those such as found in MYCOTAXON, Vol. XLIV, NO. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, as well as microorganisms belonging to the subgenus *Micromucor* such as *Mortierella isabellina* CBS194.28, IFO06336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, IFO8185, IFO8287, *Mortierella vinacea* CBS236.82. Particularly preferred is *Mortierella alpina*.

When a fungus is used as a host, it is desirable that the nucleic acid of the present invention is self-replicable in the host or has a structure insertable onto the fungal chromosome. At the same time, it is preferable to further comprise a promoter and a terminator. When *M. alpina* is used as a host, examples of an expression vector include pD4, pDuraSC and pDura5. Any promoter may be used as long as it allows expression in the host, and examples include promoters derived from *M. alpina*, such as histonH4.1 gene promoter, GAPDH (glyceraldehyde-3-phosphate dehydrogenase) gene promoter and TEF (translation elongation factor) gene promoter.

Techniques for introducing a recombinant vector into filamentous fungi (e.g., *M. alpina*) include electroporation, spheroplast and particle delivery methods, as well as direct microinjection of DNA into nuclei. In the case of using an auxotrophic host strain, strains growing on a selective medium lacking nutrients required for the host strain may be selected to thereby obtain transformed strains. Alternatively, in a case where a drug resistance marker gene is used for transformation, culture may be carried out with a selective medium containing the drug to thereby obtain cell colonies resistant to the drug.

When yeast is used as a host, examples of an expression vector include pYE22m. Alternatively, commercially available yeast expression vectors such as pYES (Invitrogen) and pESC(STRATAGENE) may also be used. Yeast hosts suitable for the present invention include, but are not limited to, *Saccharomyces cerevisiae* strain EH13-15 (trp1, MATα). Examples of a promoter available for use include those derived from yeast or the like, such as GAPDH promoter, gal1 promoter and gal10 promoter.

Techniques for introducing a recombinant vector into yeast cells include lithium acetate, electroporation and spheroplast methods, as well as dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, examples of an expression vector include pGEX and pUC18 available from Pharmacia. Examples of a promoter available for use include those derived from *E. coli*, phage or the like, such as trp promoter, lac promoter, PL promoter and PR promoter. Techniques for introducing a recombinant vector into bacteria include electroporation and calcium chloride methods.

Method of the Present Invention for Preparing a Fatty Acid Composition

The present invention provides a method for preparing a fatty acid composition from the above transformant, i.e., a method for preparing a fatty acid composition from a cultured product obtained by culturing the above transformant, more specifically as described below. However, the method of the present invention is not limited to the following, and may be accomplished in any other manner generally known.

For culture of organisms transformed to express GPAT, any medium may be used as long as it is a culture solution (medium) having appropriate pH and osmotic pressure as well as containing nutrients required for growth of each host, trace elements, and biomaterials such as serum or antibiotics. For example, in the case of yeast cells transformed to express GPAT, SC-Trp medium, YPD medium, YPD5 medium or the like may be used without being limited thereto. Detailed medium composition is illustrated for SC-Trp medium: 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil) per liter of medium.

Any culture conditions may be used as long as they are suitable for host growth and are adequate for maintenance of the generated enzyme in a stable state. More specifically, individual conditions may be adjusted, including anaerobic degree, culture period, temperature, humidity, static culture or shaking culture. Culture may be accomplished under the same conditions (one-step culture) or by so-called two-step or three-step culture using two or more different culture conditions. For large-scale culture, two-step or more step culture is preferred because of its high culture efficiency.

To explain detailed procedures for the method of the present invention for preparing a fatty acid composition, two-step culture in which yeast is used as a host will be illustrated below as an example. Namely, in the pre-culture step, the colonies obtained above are inoculated into any medium described above (e.g., SC-Trp medium) and cultured with shaking at 30° C. for 2 days. Then, in the main culture step, the pre-cultured solution (500 μl) is added to 10 ml YPD5 (2% yeast extract, 1% polypeptone, 5% glucose) medium and cultured with shaking at 30° C. for 2 days.

Fatty Acid Compositions of the Present Invention

The present invention also provides a fatty acid composition which is a collection of one or more fatty acids in cells expressing GPAT2 of the present invention. Fatty acids may be free fatty acids or may be triglycerides, phospholipids or the like. In particular, the fatty acid composition of the present invention is characterized by having a fatty acid rate ensuring a higher ratio of at least one or more of:

i) the oleic acid content;

ii) the ratio of the oleic acid content to the palmitic acid content;

iii) the ratio of the total content of stearic acid and oleic acid to the palmitic acid content; and iv) the ratio of the $C_{18}$ fatty acid content to the $C_{16}$ fatty acid content when compared to a cultured product obtained by culturing a host which is not transformed with the recombinant vector of the present invention. The phrase "host which is not transformed with the recombinant vector of the present invention" as used herein is intended to mean, for example, a host transformed with an empty vector carrying none of the nucleic acids described in the section "Nucleic acids of the present invention encoding glycerol-3-phosphate acyltransferase."

Fatty acids contained in the fatty acid composition of the present invention refer to linear or branched monocarboxylic acids of long-chain carbohydrates, including but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetradocosanoic acid) (24:0), nervonic acid (cis-15-tetradocosanoic acid) (24:1) and cerotic acid (hexadocosanoic acid) (26:0). It should be noted that the above substance names are common names defined by the IUPAC Biochemical Nomenclature, and their systematic names are given in parentheses along with numerics denoting the number of carbons and the positions of double bonds.

The fatty acid composition of the present invention may be composed of any number and any type of fatty acids, as long as it is a combination of one or more fatty acids selected from those listed above.

Whether such a fatty acid composition of the present invention is obtained, i.e., whether GPAT2 of the present invention is expressed may be confirmed in a manner generally known, for example, as a change in fatty acid rate when GPAT is expressed in yeast cells. Namely, to lyophilized cells obtained by the above method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography.

As a result, if a fatty acid composition having the above fatty acid rate is obtained, it can be determined that the fatty acid composition of the present invention was obtained. It should be noted that the GPAT of the present invention yields a fatty acid rate different from that of known GPAT fatty acid compositions, indicating that the GPAT of the present invention has substrate specificity different from that of known GPATs.

Food or Other Products Comprising Fatty Acid Compositions of the Present Invention The present invention also provides a food product comprising the above fatty acid composition. The fatty acid composition of the present invention can be used in a routine manner for purposes such as production of food products containing fats and oils as well as production of industrial source materials (those for cosmetics, pharmaceuticals (e.g., external preparations for skin), soaps, etc.). Cosmetics (cosmetic compositions) or pharmaceuticals (pharmaceutical compositions) may be formulated into any dosage form including, but not limited to, solutions, pastes, gels, solids or powders. Likewise, possible forms of food products include pharmaceutical formulations such as capsules, as well as processed foods such as ordinary fluid diets, semi-digested nourishing diets, elemental diets, drinkable preparations or enteral nutrient preparations, which comprise the fatty acid composition of the present invention in admixture with proteins, sugars, fats, trace elements, vitamins, emulsifiers, flavorings, etc.

Moreover, examples of the food product of the present invention include, but are not limited to, nutritional supplementary foods, health foods, functional foods, children's foods, infant modified milk, premature infant modified milk, and geriatric foods. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods. The term "infant modified milk" refers to modified milk given to children up to about one year old. The term "premature infant modified milk" refers to modified milk given to premature infants until about 6 months after birth.

These food products include natural foods (treated with fats and oils) such as meat, fish and nuts; foods supplemented with fats and oils during preparation (e.g., Chinese foods, Chinese noodles, soups); foods prepared using fats and oils as heating media (e.g., tempura (deep-fried fish and vegetables), deep-fried foods, fried bean curd, Chinese fried rice, doughnuts, Japanese fried dough cookies (karinto)); fat- and oil-based foods or processed foods supplemented with fats and oils during processing (e.g., butter, margarine, mayonnaise, dressing, chocolate, instant noodles, caramel, biscuits, cookies, cake, ice cream); and foods sprayed or coated with fats and oils upon finishing (e.g., rice crackers, hard biscuits, sweet bean paste bread). However, the food product of the present invention is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine (sake), medicinal liquor, sweet cooking sherry (mirin), vinegar, soy sauce and miso (bean paste); livestock food products such as yogurt, ham, bacon and sausage; seafood products such as fish cake (kamaboko), deep-fried fish cake (ageten) and puffy fish cake (hanpen); as well as fruit drinks, soft drinks, sports drinks, alcoholic beverages, and tea.

Method for Strain Evaluation or Selection Using GPAT-Encoding Nucleic Acid or GPAT Protein of the Present Invention The present invention also provides a method for evaluating or selecting a lipid-producing strain using the GPAT-encoding nucleic acid or GPAT protein of the present invention. Details are given below.

(1) Evaluation Method

One embodiment of the present invention is a method for evaluating a lipid-producing strain using the GPAT-encoding nucleic acid or GPAT protein of the present invention. As a first example for the above evaluation method of the present invention, lipid-producing test strains are evaluated for the above activity of the present invention by using primers or probes designed based on the nucleotide sequence of the present invention. General procedures for such evaluation are known and can be found in, e.g., International Patent Publication No. WO01/040514 or JP 8-205900 A. A brief explanation will be given below of this evaluation.

First, the genome of a test strain is prepared. For genome preparation, it is possible to use any known technique such as Hereford method or potassium acetate method (see, e.g., Methods in Yeast Genetics, Cold Spring Harbor Laboratory Press, p 130 (1990)).

Primers or probes are designed based on the nucleotide sequence of the present invention, preferably SEQ ID NO: 4. These primers or probes may be any regions of the nucleotide sequence of the present invention, and known procedures may be used for their design. The number of nucleotides in a polynucleotide used as a primer is generally 10 nucleotides or more, preferably 15 to 25 nucleotides. Likewise, the number of nucleotides appropriate for a region to be flanked by primers is generally 300 to 2000 nucleotides.

The primers or probes prepared above are used to examine whether the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence located upstream or downstream of this sequence or a polynucleotide comprising a nucleotide sequence complementary to the above nucleotide sequence is used as the other primer to amplify nucleic acids from the test strain by PCR or other techniques, followed by determining the presence or absence of amplification products, the molecular weight of amplification products, etc.

PCR conditions suitable for the method of the present invention are not limited in any way, and may be set as follows, by way of example:
  Denaturation temperature: 90-95° C.
  Annealing temperature: 40-60° C.
  Elongation temperature: 60-75° C.
  Number of cycles: 10 or more cycles.

The resulting reaction products may be separated by electrophoresis on an agarose gel or the like to determine the molecular weight of the amplification products. Each amplification product is then confirmed as to whether its molecular weight is a size enough to cover a nucleic acid molecule corresponding to a region specific to the nucleotide sequence of the present invention, whereby the test strain can be predicted or evaluated for the above activity of the present invention. Moreover, if the above amplification products are analyzed for their nucleotide sequences, as described above, the above activity of the present invention can be predicted or evaluated with more accuracy. It should be noted that procedures for evaluating the above activity of the present invention are as described above.

As another example for the above evaluation method of the present invention, a test strain is cultured and measured for the expression level of GPAT encoded by the nucleotide sequence of the present invention (e.g., SEQ ID NO: 4), whereby the test strain can be evaluated for the above activity of the present invention. It should be noted that the expression level of GPAT can be measured by culturing a test strain under appropriate conditions and quantifying mRNA or protein for GPAT. Quantification of mRNA or protein may be accomplished by using known procedures, for example, Northern hybridization or quantitative RT-PCR for mRNA quantification and Western blotting for protein quantification (Current Protocols in Molecular Biology, John Wiley & Sons 1994-2003). For evaluation of the above activity, it is also possible to measure the fatty acid rate of a fatty acid composition produced by the GPAT of the present invention. Procedures for measuring the fatty acid rate of a fatty acid composition are as described above.

(2) Selection Method

Another embodiment of the present invention is a method for selecting a lipid-producing strain using the GPAT-encoding nucleic acid or GPAT protein of the present invention. As an example for the above selection method of the present invention, test strains are cultured and measured for the expression level of GPAT encoded by the nucleotide sequence of the present invention (e.g., SEQ ID NO: 4) to select a strain with a desired expression level, whereby a strain having a desired activity can be selected. Alternatively, a type strain is predetermined, and this type strain and test strains are each cultured and measured for the above expression level, followed by comparison of the expression level between the type strain and each test strain, whereby a desired strain can be selected. More specifically, for example, a type strain and test strains are cultured under appropriate conditions and measured for their expression levels to select a test strain showing higher or lower expression than the type strain, whereby a strain having a desired activity can be selected. Examples of a desired activity include the expression level of GPAT and the fatty acid rate of a fatty acid composition produced by GPAT, which may be measured as described above.

As another example for the above selection method of the present invention, test strains are cultured to select a strain in which the above activity of the present invention is high or low, whereby a strain having a desired activity can be selected. Examples of a desired activity include the expression level of GPAT and the fatty acid rate of a fatty acid composition produced by GPAT, which may be measured as described above.

Examples of a test strain or type strain available for use include, but are not limited to, a strain transformed with the above vector of the present invention, a strain modified to suppress expression of the above nucleic acid of the present invention, a strain modified by mutagenesis, and a strain having natural mutation(s). It should be noted that GPAT activity in the present invention and the ability to yield the fatty acid rate of GPAT in the present invention can be measured, for example, by the procedures described in the sections "Nucleic acids of the present invention encoding glycerol-3-phosphate acyltransferase" and "Fatty acid compositions of the present invention." Mutagenesis may be accomplished by, but not limited to, physical techniques including ultraviolet or radioactive irradiation, or chemical techniques including treatment with an agent such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Strains used in the present invention as type and test strains include, but are not limited to, the above lipid-producing strains or yeast strains. More specifically, the type strain or test strain may be a combination of any strains belonging to different genera or species, and one or more test strains may be used simultaneously.

The present invention will now be described in more detail by way of the following examples, which are not intended to limit the scope of the invention.

Example 1

(1) EST Analysis

*M. alpina* strain 1S-4 was inoculated into 100 ml medium (1.8% glucose, 1% yeast extract, pH 6.0) and pre-cultured for 3 days at 28° C. A 10 L culture vessel (Able Co., Tokyo) was charged with 5 L medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using an Oligotex-dT30<Super>mRNA Purification Kit (Takara Bio Inc., Japan), poly(A)$^+$RNA was purified from the total RNA. A cDNA library was prepared for each stage with a ZAP-cDNA Synthesis Kit (STRATAGENE), followed by one-pass sequence analysis from the 5'-end of cDNA (8000 clones×5 stages). The resulting sequences were clustered. As a result, about 5000 sequences were obtained.

(2) Search for GPAT Gene Homologs

The nucleotide sequences obtained from EST analysis were searched against amino acid sequences registered in GENBANK with a homology search program, BLASTX, to extract homologs of the GPAT gene. As a result, one GPAT homolog sequence (SEQ ID NO: 5) was found.

A protein showing the highest identity during the above search was *S. cerevisiae*-derived glycerol-3-phosphate acyltransferase Sct1p (which is a protein encoded by YBL011w).

A GPAT homolog from *M. alpina* has already been shown in US Patent Publication No. US2006/0094091. When this known *M. alpina*-derived sequence (hereinafter referred to as GPAT1) was compared with the sequence obtained above, GPAT1 shared no significant identity with SEQ ID NO: 5. Thus, SEQ ID NO: 5 appeared to be an EST of another homolog distinct from the known *M. alpina* GPAT, and this GPAT homolog was referred to as GPAT2.

Example 2

(1) Cloning of GPAT Homologs

SEQ ID NO: 5 contains no CDS appearing to encode a GPAT homolog. Thus, for cloning of cDNA encoding the full length of this gene, primers were prepared based on SEQ ID NO: 5 as follows.
Primers designed based on SEQ ID NO: 5:

```
Primer E-1:
CTGACTACCAAAACCAGCTGGACTTC      (SEQ ID NO: 6)

Primer E-2:
GGCAATTTCATCCAAGTTGTCCTCC       (SEQ ID NO: 7)
```

Using this primer pair, PCR was performed with ExTaq (Takara Bio Inc., Japan) by using the cDNA library on day 8 containing ESTs constituting SEQ ID NO: 5 as a template. The resulting DNA fragments were TA-cloned with a TOPO-TA cloning Kit (INVITROGEN CORPORATION) to determine the nucleotide sequence of an insert.

The results confirmed that a DNA fragment comprising a nucleotide sequence covering nucleotides 5-243 of SEQ ID NO: 5 was cloned. This plasmid was designated as pCR-E-P. Then, this plasmid was used as a template to perform PCR with the above primers. In PCR, ExTaq (Takara Bio Inc., Japan) was used, but the attached dNTP mix was replaced by a PCR labeling mix (Roche Diagnostics) for digoxigenin (DIG) labeling of DNA to be amplified, thereby preparing a probe for use in cDNA library screening. This probe was used to screen the cDNA library from which the ESTs constituting SEQ ID NO: 5 had been obtained by EST analysis.

Hybridization conditions were set as follows.
Buffer: 5×SSC, 1% SDS, 50 mM Tris-HCl (pH 7.5), 50% formamide
Temperature: 42° C. (overnight)
Washing: in 0.2×SSC, 0.1% SDS at 65° C. for 20 minutes (repeated three times)

Detection was accomplished by using a DIG nucleic acid detection kit (Roche Diagnostics). From phage clones obtained by screening, the plasmid was excised by in vivo excision to obtain plasmid DNA.

The nucleotide sequence of an insert from a clone obtained by screening of cDNA containing SEQ ID NO: 5 is shown in SEQ ID NO: 1. SEQ ID NO: 1 contains a CDS of 1779 bp between positions 113 and 1891, thus suggesting that a sequence encoding the full length of GPAT homolog (GPAT2) was obtained. The deduced amino acid sequence of a protein encoded by this gene is shown in SEQ ID NO: 2. The plasmid containing SEQ ID NO: 1 was designated as pB-GPAT2.

On the other hand, for cloning of GPAT1 derived from *M. alpina* strain 1S-4, the following primers were prepared based on the ORF sequence of GPAT homolog shown in SEQ ID NO: 1 of US Patent Publication No. 2006/0094091.

```
Primer GPAT1-1
ggatccatggcccttcagatctacga      (SEQ ID NO: 8)

Primer GPAT1-2
gtcgacctaaatgtcttttgacttggc     (SEQ ID NO: 9)
```

The underlined regions in the above primers are restriction enzyme recognition sites which were added.

Using these primers, PCR was performed with KOD-Plus- (Toyobo Co., Ltd., Japan) by using a cDNA library as a template. The amplified fragments were subcloned into pCR4Blunt-TOPO (Invitrogen) and confirmed for their nucleotide sequences. A clone appearing to have the correct nucleotide sequence of this gene was designated as pCR4-GPAT1. The thus cloned cDNA nucleotide sequence of GPAT1 derived from *M. alpina* strain 1S-4 is shown in SEQ ID NO: 10, and the deduced amino acid sequence of GPAT1 encoded by this cDNA is shown in SEQ ID NO: 11.

(2) Sequence Analysis

The thus obtained cDNA sequence of *M. alpina*-derived GPAT homolog (GPAT2) was subjected to BLASTX homology analysis against amino acid sequences registered in GENEBANK. As a result, an amino acid sequence having the lowest E-value, i.e., sharing the highest identity with the sequence of this homolog was an *Aspergillus nidulans*-derived 1-acyl-sn-glycerol-3-phosphate acyltransferase-like putative protein sequence (GB Accession No. EAA62242). Among proteins whose functions have been clarified, a protein showing the highest identity was *Saccharomyces cerevisiae*-derived glycerol-3-phosphate acyltransferase Sct1p (GB Accession No. CAC85390). The above sequences sharing the highest identity were analyzed by clustalW to determine their identity with ORF of this homolog sequence at the nucleotide and amino acid sequence levels. As a result, they were found to have an identity of 36.9% and 36.6% at the nucleotide sequence level and 17.0% and 15.0% at the amino acid sequence level, respectively.

Neither the cloned nucleotide sequence of SEQ ID NO: 1 nor its deduced amino acid sequence of SEQ ID NO: 2 shared significantly high identity with known nucleotide sequences and amino acid sequences, thus suggesting that the cloned nucleotide sequence and its deduced amino acid sequence would be novel GPAT derived from *M. alpina*.

In contrast, the above cloned GPAT1 derived from *M. alpina* strain 1S-4 (whose cDNA and deduced amino acid sequences are shown in SEQ ID NOs: 10 and 11, respectively) was compared with GPAT1 derived from *M. alpina* (ATCC #16266) (US Patent Publication No. 2006/0094091), confirming that there was an identity of 90.4% at the nucleotide sequence level and 97.9% at the amino acid sequence level.

Example 3

Construction of Yeast Expression Vector

To express GPAT2 in yeast cells, a yeast expression vector was constructed as follows. Namely, the plasmid pB-GPAT2 was digested with a restriction enzyme KpnI and then partially digested with a restriction enzyme SadI to obtain a DNA fragment of approximately 2 kb. This DNA fragment was inserted into the SacI-KpnI site of yeast expression vector pYE22m (Biosci. Biotech. Biochem., 59, 1221-1228, 1995) to construct plasmid pYE-MAGPAT2.

On the other hand, to express GPAT1 in yeast cells, a yeast expression vector was constructed as follows. The plasmid pCR4-GPAT1 was digested with restriction enzymes BamHI and SalI to obtain a DNA fragment of approximately 2.2 kb. This DNA fragment was inserted into the BamHI-SalI site of yeast expression vector pYE22m (Biosci. Biotech. Biochem., 59, 1221-1228, 1995) to construct plasmid pYE-MAGPAT1.

Example 4

Yeast Transformation

The plasmid pYE22m, pYE-MAGPAT1 or pYE-MAGPAT2 was used to transform yeast *Saccharomyces cerevisiae* strain EH13-15 (trp1, MATα) (Appl. Microbiol. Biotechnol., 30, 515-520, 1989) by the lithium acetate method. The transformed strains were screened by the ability to grow on SC-Trp agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Example 5

Yeast Culture

Among the transformed strains obtained with each yeast expression vector, any two strains (strains c-1 and c-2, strains GPAT1-1 and GPAT1-2, or strains GPAT2-1 and GPAT2-2) were selected and cultured under the following conditions.

Namely, in the pre-culture step, a loopful of each yeast strain was inoculated from the plate into SC-Trp medium (10 ml) and cultured with shaking at 30° C. for 2 days. In the main culture step, the pre-cultured solution (500 μl) was added to 10 ml YPD5 (2% yeast extract, 1% polypeptone, 5% glucose) medium and cultured with shaking at 30° C. for 2 days.

Example 6

Fatty Acid Analysis of Yeast Strains

The cultured yeast solutions were each centrifuged to collect the cells. After washing with 10 ml sterilized water, the cells were collected again by centrifugation and lyophilized. To the lyophilized cells, chloroform:methanol (2:1, 4 ml) was added and stirred vigorously, followed by incubation at 70° C. for 1 hour. The cells were separated by centrifugation to collect the solvent. To the remaining cells, chloroform:methanol (2:1, 4 ml) was added again, and the same procedure was repeated to collect the solvent. After lipids were dried up with a SpeedVac, 2 ml chloroform was added to dissolve the lipids. A 200 μl aliquot of this sample was treated by the hydrochloric acid/methanol method to derive fatty acids in the cells into corresponding methyl esters, followed by extraction with hexane. After distilling off hexane, the fatty acids were analyzed by gas chromatography.

The results obtained are shown in Table 2.

TABLE 2

Fatty acid rate of transformed strains (host: EH13-15)

| Sample name | c-1 | c-2 | GPAT1-1 | GPAT1-2 | GPAT2-1 | GPAT2-2 |
|---|---|---|---|---|---|---|
| 16:0 | 6.14 | 6.16 | 7.37 | 7.28 | 4.77 | 4.82 |
| 16:1 | 39.75 | 39.49 | 37.59 | 37.77 | 33.62 | 34.53 |
| 18:0 | 4.50 | 4.51 | 4.85 | 5.09 | 5.73 | 5.30 |
| 18:1 | 45.70 | 46.08 | 45.87 | 46.26 | 51.76 | 51.09 |
| other | 3.91 | 3.77 | 4.33 | 3.60 | 4.12 | 4.27 |
| 16:1/16:0 | 6.47 | 6.41 | 5.10 | 5.19 | 7.04 | 7.16 |
| 18:1/16:0 | 7.44 | 7.48 | 6.23 | 6.36 | 10.84 | 10.60 |
| (18:0 + 18:1)/16:0 | 8.17 | 8.21 | 6.89 | 7.06 | 12.04 | 11.70 |
| (18:0 + 18:1)/(16:0 + 16:1) | 1.09 | 1.11 | 1.13 | 1.14 | 1.50 | 1.43 |

The yeast strains transformed with two GPAT homologs derived from *M. alpina* and the control yeast strains were compared for their fatty acid rate. In the fatty acid rate of the GPAT1-transformed yeast, the percentage of palmitic acid increased, but the palmitoleic acid content decreased when compared to the control strains. Stearic acid and oleic acid were in the same percentages as in the control strains. Thus, the ratio of the palmitoleic acid content to the palmitic acid content, the ratio of the oleic acid content to the palmitic acid content, and the ratio of the total content of stearic acid and oleic acid to the palmitic acid content were lower than those of the control strains.

In contrast, in the GPAT2-transformed yeast, the percentage of oleic acid increased by 10% or more when compared to the control strains. The percentages of palmitic acid and palmitoleic acid both decreased when compared to the control strains, whereas the ratio of the palmitoleic acid content to the palmitic acid content increased slightly when compared to the control strains. Moreover, in the GPAT2-transformed yeast, the ratio of the oleic acid content to the palmitic acid content and the ratio of the total content of stearic acid and oleic acid to the palmitic acid content both increased when compared to the control strains. Further, in the GPAT2-transformed yeast, the ratio of $C_{18}$ fatty acids to $C_{16}$ fatty acids increased, indicating that fatty acids with longer chain lengths were produced.

These results indicated that two GPAT homologs derived from *M. alpina* had different specificity for their substrate acyl group, and hence yeast strains transformed with these genes yielded different fatty acid rates from homolog to homolog. The results also indicated that it was possible to breed organisms with a desired fatty acid rate when the above homologs were selected to suit the intended purpose.

Example 7

Expression Analysis in Arachidonic Acid-Producing Yeast Strains (1) Breeding of Arachidonic Acid-Producing Yeast Strains To breed arachidonic acid-producing yeast (*Saccharomyces cerevisiae*) strains, the following plasmids were constructed.

First, cDNA prepared from *M. alpina* strain 1S-4 was used as a template to perform PCR with ExTaq using a primer set of Δ12-f and Δ12-r, Δ6-f and Δ6-r, GLELO-f and GLELO-r, or Δ5-f and Δ5-r to thereby amplify the Δ12 fatty acid desaturase gene, the Δ6 fatty acid desaturase gene, the GLELO fatty acid elongase gene or the Δ5 fatty acid desaturase gene in the *M. alpina* strain 1S-4.

Δ12-f:
TCTAGAATGGCACCTCCCAACACTATTG    (SEQ ID NO: 12)

Δ12-r:
AAGCTTTTACTTCTTGAAAAAGACCACGTC    (SEQ ID NO: 13)

Δ6-f:
TCTAGAATGGCTGCTGCTCCCAGTGTGAG    (SEQ ID NO: 14)

Δ6-r:
AAGCTTTTACTGTGCCTTGCCCATCTTGG    (SEQ ID NO: 15)

GLELO-f:
TCTAGAATGGAGTCGATTGCGCAATTCC    (SEQ ID NO: 16)

GLELO-r:
GAGCTCTTACTGCAACTTCCTTGCCTTCTC    (SEQ ID NO: 17)

Δ5-f:
TCTAGAATGGGTGCGGACACAGGAAAAACC    (SEQ ID NO: 18)

Δ5-r:
AAGCTTTTACTCTTCCTTGGGACGAAGACC    (SEQ ID NO: 19)

These genes were cloned with a TOPO-TA-cloning Kit. The clones were confirmed for their nucleotide sequences, and those containing the nucleotide sequences of SEQ ID NOs: 20-23 were designated as plasmids pCR-MAΔ12DS (containing the nucleotide sequence of SEQ ID NO: 20), pCR-MAΔ6DS (containing the nucleotide sequence of SEQ ID NO: 21), pCR-MAGLELO (containing the nucleotide sequence of SEQ ID NO: 22) and pCR-MAΔ5DS (containing the nucleotide sequence of SEQ ID NO: 23), respectively.

On the other hand, a HindIII-digested DNA fragment of approximately 1.2 kb obtained from plasmid pURA34 (JP 2001-120276 A) was inserted into the HindIII site of vector pUC18 which had been digested with restriction enzymes EcoRI and SphI, followed by blunt ending and self-ligation. A clone in which the EcoRI site of the vector was on the 5'-side of URA3 was designated as pUC-URA3. Likewise, a SalI- and XhoI-digested DNA fragment of approximately 2.2 kb obtained from YEp13 was inserted into the SalI site of vector pUC18, and a clone in which the EcoRI site of the vector was on the 5'-side of LUE2 was designated as pUC-LEU2.

Next, the plasmid pCR-MAΔ12DS was digested with a restriction enzyme HindIII and, after blunt ending, was further digested with a restriction enzyme XbaI to obtain a DNA fragment of approximately 1.2 kbp, while vector pESC-URA (STRATAGENE) was digested with a restriction enzyme SacI and, after blunt ending, was further digested with a restriction enzyme SpeI to obtain a DNA fragment of approximately 6.6 kbp. These DNA fragments were ligated to obtain plasmid pESC-U-Δ12. The plasmid pCR-MAΔ6DS was digested with a restriction enzyme XbaI and, after blunt ending, was further digested with a restriction enzyme HindIII to obtain a DNA fragment of approximately 1.6 kbp, while the plasmid pESC-U-Δ12 was digested with a restriction enzyme SalI and, after blunt ending, was further digested with a restriction enzyme HindIII to obtain a DNA fragment of approximately 8 kbp. These DNA fragments were ligated to obtain plasmid pESC-U-Δ12:Δ6. This plasmid was partially digested with a restriction enzyme PvuII, and the resulting fragment of approximately 4.2 kb was inserted into the SmaI site of pUC-URA3 to obtain plasmid Puc-URA-Δ12:Δ6.

Likewise, the plasmid pCR-MAGLELO was digested with restriction enzymes XbaI and SacI to obtain a DNA fragment of approximately 0.95 kbp, while vector pESC-LEU (STRATAGENE) was digested with restriction enzymes XbaI and SacI to obtain a DNA fragment of approximately 7.7 kbp. These DNA fragments were ligated to obtain plasmid pESC-L-GLELO. The plasmid pCR-MAΔ5DS was digested with a restriction enzyme XbaI and, after blunt ending, was further digested with a restriction enzyme HindIII to obtain a DNA fragment of approximately 1.3 kbp, while the plasmid pESC-L-GLELO was digested with a restriction enzyme ApaI and, after blunt ending, was further digested with a restriction enzyme HindIII to obtain a DNA fragment of approximately 8.7 kbp. These DNA fragments were ligated to obtain plasmid pESC-L-GLELO:Δ5. This plasmid was digested with a restriction enzyme PvuII, and the resulting fragment of approximately 3.2 kb was inserted into the SmaI site of pUC-LEU2 to obtain plasmid pUC-LEU-GLELO:Δ5. *S. cerevisiae* strain YPH499 (STRATAGENE) was co-transformed with plasmid pUC-URA-Δ12:Δ6 and plasmid pUC-LEU-GLELO:Δ5. The transformed strains were screened by the ability to grow on SC-Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, 6 g threonine and 1.2 g tryptophan). Among the strains thus obtained, any one strain was designated as strain ARA3-1.

(2) Obtaining and Analysis of Transformed Strains of Arachidonic Acid-Producing Yeast The strain ARA3-1 was transformed respectively with plasmids pYE22m, pYE-MAGPAT1 and pYE-MAGPAT2. The transformed strains were screened by the ability to grow on SC-Trp,Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine). Among the strains thus transformed, any 4 strains were selected for each plasmid.

These strains were each cultured at 30° C. for 1 day in the above SC-Trp,Leu,Ura liquid medium (10 ml), 1 ml of which was then cultured at 15° C. for 7 days in SG-Trp,Leu,Ura liquid medium (10 ml) containing, per liter, 6.7 g Yeast nitrogen base w/o amino acids (DIFCO), 20 g galactose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine), followed by analysis of fatty acids in the cells. Tables 3 and 4 show the fatty acid rate in the cells and the fat and oil content in the cells, respectively.

TABLE 3

| Intracellular fatty acid content (%) | | |
|---|---|---|
| control | GPAT1 | GPAT2 |
| 6.32 ± 0.59 | 6.50 ± 0.31 | 8.08 ± 0.38 |

Mean ± SD

TABLE 4

Ratio (%) of DGLA or ARA to total fatty acid

| | control | GPAT1 | GPAT2 |
|---|---|---|---|
| DGLA | 0.33 ± 0.02 | 0.32 ± 0.07 | 0.50 ± 0.05 |
| ARA | 0.44 ± 0.03 | 0.46 ± 0.09 | 0.55 ± 0.06 |

Mean ± SD

In a case where *M. alpina*-derived GPAT2 was expressed in arachidonic acid-producing yeast cells, the ratios of PUFAs including DGLA and arachidonic acid were increased when compared to the control. Likewise, the intracellular fatty acid content was also increased.

Example 8

Vector Construction for *M. Alpina* Expression

The vectors used for *M. alpina* expression were pDuraSC which allows expression of a desired gene from the GAPDH promoter, and pDuraMCS which allows expression of a desired gene from the histone promoter.

To express GPAT2 in *M. alpina* cells, vectors were constructed as follows. The plasmid pB-GPAT2 was digested with a restriction enzyme PstI and then partially digested with a restriction enzyme XhoI. Among the resulting DNA fragments, a fragment of approximately 1.7 kb was excised and inserted between the PstI and XhoI site in the multicloning site of vector pDuraSC or pDura5MCS. The resulting constructs were designated as plasmids pDuraSC-GPAT2 and pDura5MCS-GPAT2, respectively.

Obtaining of Transformed *M. Alpina* Strains

Uracil-auxotrophic strain Aura-3 derived from *M. alpina* as described in a patent document (WO2005/019437 entitled "Method of Breeding Lipid-Producing Fungus") was used as a host and transformed with these plasmids by the particle delivery method. For screening of the transformed strains, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

Evaluation of *M. Alpina* Transformants

The resulting transformed strains were each inoculated into 4 ml GY medium (2% glucose, 1% yeast extract) and cultured with shaking at 28° C. for 3 or 4 days. The cells were collected by filtration, and RNA was extracted with an RNeasy plant kit (QIAGEN). A SuperScript First-Strand system for RT-PCR (Invitrogen) was used to synthesize cDNA. To confirm expression from the introduced construct and total expression for each gene, RT-PCR was performed with the following primer sets.

Strains Transformed with Plasmid pDuraSC-GPAT2
Primers used for confirmation of expression from the introduced construct:

```
MaGAPDHpfw:
CACACCACACATTCAACATC;       (SEQ ID NO: 24)
and

E2:
GGCAATTTCATCCAAGTTGTCCTCC   (SEQ ID NO: 25)
```

Primers used for confirmation of total GPAT2 expression:

```
E1:
CTGACTACCAAAACCAGCTGGACTTC;  (SEQ ID NO: 26)
and E2
```

Strains Transformed with Plasmid pDura5MCS-GPAT2
Primers used for confirmation of expression from the introduced construct:

```
                                            (SEQ ID NO: 27)
PD4P: CGCATCCCGCAAACACACAC and primer E2,
```

Primers used for confirmation of total GPAT2 expression:
Primers E1 and E2

Based on the results of the above RT-PCR, transformants showing high level expression of each gene both in expression from the introduced construct and in total expression were selected: strains Gp-GPAT2-30 and Hp-GPAT2-9 from those transformed with plasmids pDuraSC-GPAT2 and pDura5MCS-GPAT2, respectively.

These strains were each inoculated into GY medium (4 ml) and cultured with shaking at 28° C. at 125 rpm. On day 3 of culture, 20% glucose (400 μl) was added and culture was further continued. Alternatively, on day 6 of culture, all cells were collected by filtration and lyophilized. A portion (about 10-20 mg) of the dried cells was treated by the hydrochloric acid/methanol method to derive fatty acids in the cells into corresponding methyl esters, followed by extraction with hexane. After distilling off hexane, the fatty acids were analyzed by gas chromatography. The intracellular fatty acid content and the arachidonic acid production per medium are summarized in Tables 5 and 6, respectively.

TABLE 5

Intracellular fatty acid content (%)

| Gp-G2-30 | Hp-G2-9 | B2BB |
|---|---|---|
| 34.60 ± 1.17 | 35.05 ± 0.86 | 30.98 ± 3.24 |

Mean ± SD

TABLE 6

Arachidonic acid production (g/L) per medium

| Gp-G2-30 | Hp-G2-9 | B2BB |
|---|---|---|
| 2.27 ± 0.27 | 2.39 ± 0.16 | 1.88 ± 0.27 |

Mean ± SD

As shown above, high expression of the GPAT2 gene in *M. alpina* allowed an increase in both intracellular fatty acid content and arachidonic acid production per medium.

Sequence Listing Free Text
  SEQ ID NO: 6: primer
  SEQ ID NO: 7: primer
  SEQ ID NO: 8: primer
  SEQ ID NO: 9: primer
  SEQ ID NO: 12: primer
  SEQ ID NO: 13: primer
  SEQ ID NO: 14: primer
  SEQ ID NO: 15: primer
  SEQ ID NO: 16: primer
  SEQ ID NO: 17: primer
  SEQ ID NO: 18: primer
  SEQ ID NO: 19: primer
  SEQ ID NO: 24: primer
  SEQ ID NO: 25: primer
  SEQ ID NO: 26: primer
  SEQ ID NO: 27: primer

The invention claimed is:

1. An isolated or purified nucleic acid comprising:

(a) a nucleotide sequence which encodes a protein consisting of an amino acid sequence with deletion, substitution or addition of one to ten amino acids in the amino acid sequence shown in SEQ ID NO:2, which encoded protein has glycerol-3-phosphate acyltransferase activity;

(b) a nucleotide sequence which hybridizes under conditions of 2×SSC at 65° C. and washing conditions of 0.2×SSC at 65° C. with a nucleic acid consisting of a nucleotide sequence complementary to a nucleotide sequence consisting of SEQ ID NO:4 and which encodes a protein, which encoded protein has glycerol-3-phosphate acyltransferase activity;
(c) a nucleotide sequence which consists of a nucleotide sequence sharing an identity of 90% or more with a nucleotide sequence consisting of SEQ ID NO:4 and which encodes a protein, which encoded protein has glycerol-3-phosphate acyltransferase activity;
(d) a nucleotide sequence which encodes an amino acid sequence sharing an identity of 90% or more with an amino acid sequence consisting of SEQ ID NO:2 and which encodes a protein, which encoded protein has glycerol-3-phosphate acyltransferase activity; or
(e) a nucleotide sequence which hybridizes under conditions of 2×SSC at 65° C. and washing conditions of 0.2×SSC at 65° C. with a nucleic acid consisting of a nucleotide sequence complementary to a nucleotide sequence encoding a polypeptide consisting of the amino acid sequence shown in SEQ ID NO:2 and which encodes a protein, which encoded protein has glycerol-3-phosphate acyltransferase activity.

2. An isolated or purified nucleic acid comprising:
(a) the nucleotide sequence shown in SEQ ID NO:4;
(b) a nucleotide sequence encoding a protein consisting of the amino acid sequence shown in SEQ ID NO:2; or
(c) the nucleotide sequence shown in SEQ ID NO:1.

3. A recombinant vector comprising the nucleic acid according to claim 1.

4. A transformant transformed with the recombinant vector according to claim 3.

* * * * *

SEQUENCE LISTING

<160> NUMBER OF SEQ ID NOS: 27

<210> SEQ ID NO 1
<211> LENGTH: 1942
<212> TYPE: DNA
<213> ORGANISM: Mortierella alpina
<220> FEATURE:
<221> NAME/KEY: CDS
<222> LOCATION: (113)..(1888)

<400> SEQUENCE: 1

```
gcttccctcc acacttccct ttccttcaac accaaaccct atccgaaccc tctgtctcat      60 tttctctct ctctccctat ctctctctct ctctatcctc acatatatcc tc atg gcc     118
                                                          Met Ala
                                                            1 aaa ctt cgg aag cgg acc tcc cag tca aag gag ggc gcc gct gac acc      166
Lys Leu Arg Lys Arg Thr Ser Gln Ser Lys Glu Gly Ala Ala Asp Thr
         5                  10                  15 aac ggc aca agg cga gac agc gtc gat gac acg aac agc gtc ggc agc      214
Asn Gly Thr Arg Arg Asp Ser Val Asp Asp Thr Asn Ser Val Gly Ser
 20                  25                  30 tac gat cca cgc gcc ctc tcc aac gat cca cca aag atg tac agg gcg      262
Tyr Asp Pro Arg Ala Leu Ser Asn Asp Pro Pro Lys Met Tyr Arg Ala
 35                  40                  45                  50 atc cgg ttc ttc ttc aag atg tgc ctg cac tcc ttc tat ggc cat gtg      310
Ile Arg Phe Phe Phe Lys Met Cys Leu His Ser Phe Tyr Gly His Val
                 55                  60                  65 gag gtc gag ggc acc gag aat att gca cca aac aac tac cct gct atc      358
Glu Val Glu Gly Thr Glu Asn Ile Ala Pro Asn Asn Tyr Pro Ala Ile
         70                  75                  80 ctt gtt gcg aac cac agc aac agt ttg acg gat gcg att gcc att atg      406
Leu Val Ala Asn His Ser Asn Ser Leu Thr Asp Ala Ile Ala Ile Met
     85                  90                  95 tcg act gtt cct ccc aag agc agg agc atg att agg atg acc gca aag      454
Ser Thr Val Pro Pro Lys Ser Arg Ser Met Ile Arg Met Thr Ala Lys
100                 105                 110 gac acg ttt tgg cat aag cca ggc gtc ttc aat tat gtc atc aaa aac      502
Asp Thr Phe Trp His Lys Pro Gly Val Phe Asn Tyr Val Ile Lys Asn
115                 120                 125                 130 gct ggc act gtc ccg atc aaa aga cgc aag gat tat gag aac caa aag      550
Ala Gly Thr Val Pro Ile Lys Arg Arg Lys Asp Tyr Glu Asn Gln Lys
             135                 140                 145 gtc gac aac act gac gcg atg ggt gca ttg atc gat acc ctt gga gca      598
Val Asp Asn Thr Asp Ala Met Gly Ala Leu Ile Asp Thr Leu Gly Ala
         150                 155                 160 gga agt tgt gta tgc atg ttc ccg gag ggc atc tcg cgc tat cac cca      646
Gly Ser Cys Val Cys Met Phe Pro Glu Gly Ile Ser Arg Tyr His Pro
     165                 170                 175 caa ctt gct ccg ttc aag gcc ggt gtc gcc atg att gcc agc gat acg      694
Gln Leu Ala Pro Phe Lys Ala Gly Val Ala Met Ile Ala Ser Asp Thr
180                 185                 190 ctc tcc cgg ttt caa gac acg ccc gat ttt tct ctc acg ctc atg aca      742
Leu Ser Arg Phe Gln Asp Thr Pro Asp Phe Ser Leu Thr Leu Met Thr
195                 200                 205                 210 gcg tcg atc aac tat ctt cac cgt gaa aag ttc cga tct gat gtt ctc      790
Ala Ser Ile Asn Tyr Leu His Arg Glu Lys Phe Arg Ser Asp Val
             215                 220                 225 gtc acg ttc cat gca ccc att gtg cta acc ccg caa caa gac tcg aag      838
Val Thr Phe His Ala Pro Ile Val Leu Thr Pro Gln Gln Asp Ser Lys
         230                 235                 240
```

| | | |
|---|---|---|
| ctg ttt tcg act gac ctg gaa gtc aag aag gaa gcg atc cga aaa ctg<br>Leu Phe Ser Thr Asp Leu Glu Val Lys Lys Glu Ala Ile Arg Lys Leu<br>245 250 255 | | 886 |
| aca gag ttg ctc gag ggc acc gtc cga tca act cta ctg gat gcc gag<br>Thr Glu Leu Leu Glu Gly Thr Val Arg Ser Thr Leu Leu Asp Ala Glu<br>260 265 270 | | 934 |
| gac tgg caa aca gtc cga gtg ggt cat gtt gcc agg aag ctc tat gct<br>Asp Trp Gln Thr Val Arg Val Gly His Val Ala Arg Lys Leu Tyr Ala<br>275 280 285 290 | | 982 |
| ggc gat ctg gga act cgg att tcg ctg gga cag tac gtg cgt ttg acc<br>Gly Asp Leu Gly Thr Arg Ile Ser Leu Gly Gln Tyr Val Arg Leu Thr<br>295 300 305 | | 1030 |
| agg aag ttt gtc acg gcg ttc agt cag cac aag cag gag gag gag gca<br>Arg Lys Phe Val Thr Ala Phe Ser Gln His Lys Gln Glu Glu Glu Ala<br>310 315 320 | | 1078 |
| gcg gtc gat gac gag cgt tat ggt cag gag aag cac ggg ggc ggt gcc<br>Ala Val Asp Asp Glu Arg Tyr Gly Gln Glu Lys His Gly Gly Gly Ala<br>325 330 335 | | 1126 |
| gag agg aat ggt gat tct ttg gag atg agg cat cct gag cgc atg gat<br>Glu Arg Asn Gly Asp Ser Leu Glu Met Arg His Pro Glu Arg Met Asp<br>340 345 350 | | 1174 |
| aag gcg act aga aag aaa atc gac gag ctc gcc agg gat ttg gct gac<br>Lys Ala Thr Arg Lys Lys Ile Asp Glu Leu Ala Arg Asp Leu Ala Asp<br>355 360 365 370 | | 1222 |
| tac caa aac cag ctg gac ttc tat cac ctc aag gac tat cgt atc aag<br>Tyr Gln Asn Gln Leu Asp Phe Tyr His Leu Lys Asp Tyr Arg Ile Lys<br>375 380 385 | | 1270 |
| caa ggc aag cca agt gca aag att ctt atc gga cgt ctt ttc caa aga<br>Gln Gly Lys Pro Ser Ala Lys Ile Leu Ile Gly Arg Leu Phe Gln Arg<br>390 395 400 | | 1318 |
| ttc ttg ctt gct tgc ctt ttg tcg acc att tgc att cct gga ctg ttc<br>Phe Leu Leu Ala Cys Leu Leu Ser Thr Ile Cys Ile Pro Gly Leu Phe<br>405 410 415 | | 1366 |
| ctt tgg gca cct gtg ttt atc gcc gtg aag tac aaa gag agt cag ctt<br>Leu Trp Ala Pro Val Phe Ile Ala Val Lys Tyr Lys Glu Ser Gln Leu<br>420 425 430 | | 1414 |
| agg cgc aag gga ccc ttg gag gac aac ttg gat gaa att gcc cag tac<br>Arg Arg Lys Gly Pro Leu Glu Asp Asn Leu Asp Glu Ile Ala Gln Tyr<br>435 440 445 450 | | 1462 |
| aag ttg atg atc tcg act ttc ttc ttg ccg atc atc tgg ggg ttc tgg<br>Lys Leu Met Ile Ser Thr Phe Phe Leu Pro Ile Ile Trp Gly Phe Trp<br>455 460 465 | | 1510 |
| atc gta atg acc ttg cca att gcg ctc ttt agc gcg ccg ggc atc gtt<br>Ile Val Met Thr Leu Pro Ile Ala Leu Phe Ser Ala Pro Gly Ile Val<br>470 475 480 | | 1558 |
| gtt ctg atg tgg ctt acg atc cgc tgg ctt gag gac ttg atc cac aac<br>Val Leu Met Trp Leu Thr Ile Arg Trp Leu Glu Asp Leu Ile His Asn<br>485 490 495 | | 1606 |
| gcg aaa tcg atg ttg tcc ctt ttg cga ttg ctg ttt atg acg gag gat<br>Ala Lys Ser Met Leu Ser Leu Arg Leu Leu Phe Met Thr Glu Asp<br>500 505 510 | | 1654 |
| acc atg tac tcg ttg aga gac tac cgt cag ggg ctg gcg cat cgt gtg<br>Thr Met Tyr Ser Leu Arg Asp Tyr Arg Gln Gly Leu Ala His Arg Val<br>515 520 525 530 | | 1702 |
| cac gat ttt gcg gtc gat cat ctg aag ttg cct gag gac cct gag gtt<br>His Asp Phe Ala Val Asp His Leu Lys Leu Pro Glu Asp Pro Glu Val<br>535 540 545 | | 1750 |
| ctg gtc aag gag aac aag acc aag aag gtc gac agt ggc tgg atg ggc<br>Leu Val Lys Glu Asn Lys Thr Lys Lys Val Asp Ser Gly Trp Met Gly<br>550 555 560 | | 1798 |

-continued

```
aag ttg tcg ggc agc tac ttc tcg atc aag agg aga aga aag gac      1846
Lys Leu Ser Gly Ser Tyr Phe Ser Ile Lys Arg Arg Arg Lys Asp
            565                 570                 575 tgg aac gag gtt atg cga ttg cac gat gtt tct cac tat gac          1888
Trp Asn Glu Val Met Arg Leu His Asp Val Ser His Tyr Asp
580                 585                 590 tgaagctgag atcgtccttg aataaaagca gataacgcgt ggagtaactg aggg       1942

<210> SEQ ID NO 2
<211> LENGTH: 592
<212> TYPE: PRT
<213> ORGANISM: Mortierella alpina

<400> SEQUENCE: 2

Met Ala Lys Leu Arg Lys Arg Thr Ser Gln Ser Lys Glu Gly Ala Ala
1               5                   10                  15

Asp Thr Asn Gly Thr Arg Arg Asp Ser Val Asp Thr Asn Ser Val
                20                  25                  30

Gly Ser Tyr Asp Pro Arg Ala Leu Ser Asn Asp Pro Pro Lys Met Tyr
            35                  40                  45

Arg Ala Ile Arg Phe Phe Lys Met Cys Leu His Ser Phe Tyr Gly
        50                  55                  60

His Val Glu Val Glu Gly Thr Glu Asn Ile Ala Pro Asn Asn Tyr Pro
65                  70                  75                  80

Ala Ile Leu Val Ala Asn His Ser Asn Ser Leu Thr Asp Ala Ile Ala
                85                  90                  95

Ile Met Ser Thr Val Pro Pro Lys Ser Arg Ser Met Ile Arg Met Thr
            100                 105                 110

Ala Lys Asp Thr Phe Trp His Lys Pro Gly Val Phe Asn Tyr Val Ile
        115                 120                 125

Lys Asn Ala Gly Thr Val Pro Ile Lys Arg Arg Lys Asp Tyr Glu Asn
    130                 135                 140

Gln Lys Val Asp Asn Thr Asp Ala Met Gly Ala Leu Ile Asp Thr Leu
145                 150                 155                 160

Gly Ala Gly Ser Cys Val Cys Met Phe Pro Glu Gly Ile Ser Arg Tyr
                165                 170                 175

His Pro Gln Leu Ala Pro Phe Lys Ala Gly Val Ala Met Ile Ala Ser
            180                 185                 190

Asp Thr Leu Ser Arg Phe Gln Asp Thr Pro Asp Phe Ser Leu Thr Leu
        195                 200                 205

Met Thr Ala Ser Ile Asn Tyr Leu His Arg Glu Lys Phe Arg Ser Asp
    210                 215                 220

Val Leu Val Thr Phe His Ala Pro Ile Val Leu Thr Pro Gln Gln Asp
225                 230                 235                 240

Ser Lys Leu Phe Ser Thr Asp Leu Glu Val Lys Lys Glu Ala Ile Arg
                245                 250                 255

Lys Leu Thr Glu Leu Leu Glu Gly Thr Val Arg Ser Thr Leu Leu Asp
            260                 265                 270

Ala Glu Asp Trp Gln Thr Val Arg Val Gly His Val Ala Arg Lys Leu
        275                 280                 285

Tyr Ala Gly Asp Leu Gly Thr Arg Ile Ser Leu Gly Gln Tyr Val Arg
    290                 295                 300

Leu Thr Arg Lys Phe Val Thr Ala Phe Ser Gln His Lys Gln Glu Glu
305                 310                 315                 320

Glu Ala Ala Val Asp Asp Glu Arg Tyr Gly Gln Glu Lys His Gly Gly
```

```
                  325                 330                 335
Gly Ala Glu Arg Asn Gly Asp Ser Leu Glu Met Arg His Pro Glu Arg
            340                 345                 350
Met Asp Lys Ala Thr Arg Lys Lys Ile Asp Glu Leu Ala Arg Asp Leu
        355                 360                 365
Ala Asp Tyr Gln Asn Gln Leu Asp Phe Tyr His Leu Lys Asp Tyr Arg
    370                 375                 380
Ile Lys Gln Gly Lys Pro Ser Ala Lys Ile Leu Ile Gly Arg Leu Phe
385                 390                 395                 400
Gln Arg Phe Leu Leu Ala Cys Leu Leu Ser Thr Ile Cys Ile Pro Gly
            405                 410                 415
Leu Phe Leu Trp Ala Pro Val Phe Ile Ala Val Lys Tyr Lys Glu Ser
        420                 425                 430
Gln Leu Arg Arg Lys Gly Pro Leu Glu Asp Asn Leu Asp Glu Ile Ala
    435                 440                 445
Gln Tyr Lys Leu Met Ile Ser Thr Phe Phe Leu Pro Ile Ile Trp Gly
    450                 455                 460
Phe Trp Ile Val Met Thr Leu Pro Ile Ala Leu Phe Ser Ala Pro Gly
465                 470                 475                 480
Ile Val Val Leu Met Trp Leu Thr Ile Arg Trp Leu Glu Asp Leu Ile
            485                 490                 495
His Asn Ala Lys Ser Met Leu Ser Leu Arg Leu Leu Phe Met Thr
        500                 505                 510
Glu Asp Thr Met Tyr Ser Leu Arg Asp Tyr Arg Gln Gly Leu Ala His
        515                 520                 525
Arg Val His Asp Phe Ala Val Asp His Leu Lys Leu Pro Glu Asp Pro
    530                 535                 540
Glu Val Leu Val Lys Glu Asn Lys Thr Lys Lys Val Asp Ser Gly Trp
545                 550                 555                 560
Met Gly Lys Leu Ser Gly Ser Tyr Phe Ser Ile Lys Arg Arg Arg
            565                 570                 575
Lys Asp Trp Asn Glu Val Met Arg Leu His Asp Val Ser His Tyr Asp
        580                 585                 590

<210> SEQ ID NO 3
<211> LENGTH: 1779
<212> TYPE: DNA
<213> ORGANISM: Mortierella alpina

<400> SEQUENCE: 3
atggccaaac ttcggaagcg gacctcccag tcaaaggagg gcgccgctga caccaacggc        60
acaaggcgag acagcgtcga tgacacgaac agcgtcggca gctacgatcc acgcgccctc       120
tccaacgatc caccaaagat gtacagggcg atccggttct tcttcaagat gtgcctgcac       180
tccttctatg ccatgtggaa ggtcgagggc accgagaata ttgcaccaaa caactaccct       240
gctatccttg ttgcgaacca cagcaacagt ttgacggatg cgattgccat tatgtcgact       300
gttcctccca gagcaggag catgattagg atgaccgcaa aggacacgtt ttggcataag       360
ccaggcgtct tcaattatgt catcaaaaac gctggcactg tcccgatcaa agacgcaag       420 gattatgaga accaaaaggt cgacaacact gacgcgatgg gtgcattgat cgataccctt       480
ggagcaggaa gttgtgtatg catgttcccg gagggcatct cgcgctatca cccacaactt       540
gctccgttca aggccggtgt cgccatgatt gccagcgata cgctctcccg gtttcaagac       600
acgcccgatt tttctctcac gctcatgaca gcgtcgatca actatcttca ccgtgaaaag       660
```

-continued

| | |
|---|---|
| ttccgatctg atgttctcgt cacgttccat gcacccattg tgctaacccc gcaacaagac | 720 |
| tcgaagctgt tttcgactga cctggaagtc aagaaggaag cgatccgaaa actgacagag | 780 |
| ttgctcgagg gcaccgtccg atcaactcta ctggatgccg aggactggca aacagtccga | 840 |
| gtgggtcatg ttgccaggaa gctctatgct ggcgatctgg gaactcggat ttcgctggga | 900 |
| cagtacgtgc gtttgaccag gaagtttgtc acggcgttca gtcagcacaa gcaggaggag | 960 |
| gaggcagcgg tcgatgacga gcgttatggt caggagaagc acggggcgg tgccgagagg | 1020 |
| aatggtgatt ctttggagat gaggcatcct gagcgcatgg ataaggcgac tagaaagaaa | 1080 |
| atcgacgagc tcgccaggga tttggctgac taccaaaacc agctggactt ctatcacctc | 1140 |
| aaggactatc gtatcaagca aggcaagcca agtgcaaaga ttcttatcgg acgtcttttc | 1200 |
| caaagattct tgcttgcttg cctttttgtcg accatttgca ttcctggact gttcctttgg | 1260 |
| gcacctgtgt ttatcgccgt gaagtacaaa gagagtcagc ttaggcgcaa gggacccttg | 1320 |
| gaggacaact tggatgaaat tgcccagtac aagttgatga tctcgacttt cttcttgccg | 1380 |
| atcatctggg ggttctggat cgtaatgacc ttgccaattg cgctctttag cgcgccgggc | 1440 |
| atcgttgttc tgatgtggct tacgatccgc tggcttgagg acttgatcca caacgcgaaa | 1500 |
| tcgatgttgt ccctttttgcg attgctgttt atgacggagg ataccatgta ctcgttgaga | 1560 |
| gactaccgtc aggggctggc gcatcgtgtg cacgattttg cggtcgatca tctgaagttg | 1620 |
| cctgaggacc ctgaggttct ggtcaaggag aacaagacca agaaggtcga cagtggctgg | 1680 |
| atgggcaagt tgtcgggcag ctacttctcg atcaagagga aagaagaaa ggactggaac | 1740 |
| gaggttatgc gattgcacga tgtttctcac tatgactga | 1779 |

<210> SEQ ID NO 4
<211> LENGTH: 1776
<212> TYPE: DNA
<213> ORGANISM: Mortierella alpina

<400> SEQUENCE: 4

| | |
|---|---|
| atggccaaac ttcggaagcg gacctcccag tcaaaggagg gcgccgctga caccaacggc | 60 |
| acaaggcgag acagcgtcga tgacacgaac agcgtcggca gctacgatcc acgcgccctc | 120 |
| tccaacgatc caccaaagat gtacagggcg atccggttct tcttcaagat gtgcctgcac | 180 |
| tccttctatg gccatgtgga ggtcgagggc accgagaata ttgcaccaaa caactaccct | 240 |
| gctatccttg ttgcgaacca cagcaacagt ttgacggatg cgattgccat tatgtcgact | 300 |
| gttcctccca gagcaggag catgattagg atgaccgcaa aggacacgtt ttggcataag | 360 |
| ccaggcgtct tcaattatgt catcaaaaac gctggcactg tcccgatcaa agacgcaag | 420 |
| gattatgaga accaaaaggt cgacaacact gacgcgatgg gtgcattgat cgatacccctt | 480 |
| ggagcaggaa gttgtgtatg catgttcccg gagggcatct cgcgctatca cccacaactt | 540 |
| gctccgttca aggccggtgt cgccatgatt gccagcgata cgctctcccg gtttcaagac | 600 |
| acgcccgatt tttctctcac gctcatgaca gcgtcgatca actatcttca ccgtgaaaag | 660 |
| ttccgatctg atgttctcgt cacgttccat gcacccattg tgctaacccc gcaacaagac | 720 |
| tcgaagctgt tttcgactga cctggaagtc aagaaggaag cgatccgaaa actgacagag | 780 |
| ttgctcgagg gcaccgtccg atcaactcta ctggatgccg aggactggca aacagtccga | 840 |
| gtgggtcatg ttgccaggaa gctctatgct ggcgatctgg gaactcggat ttcgctggga | 900 |
| cagtacgtgc gtttgaccag gaagtttgtc acggcgttca gtcagcacaa gcaggaggag | 960 |
| gaggcagcgg tcgatgacga gcgttatggt caggagaagc acggggcgg tgccgagagg | 1020 |

```
aatggtgatt ctttggagat gaggcatcct gagcgcatgg ataaggcgac tagaaagaaa      1080
atcgacgagc tcgccaggga tttggctgac taccaaaacc agctggactt ctatcacctc      1140
aaggactatc gtatcaagca aggcaagcca agtgcaaaga ttcttatcgg acgtcttttc      1200
caaagattct tgcttgcttg ccttttgtcg accatttgca ttcctggact gttcctttgg      1260
gcacctgtgt ttatcgccgt gaagtacaaa gagagtcagc ttaggcgcaa gggacccttg      1320
gaggacaact tggatgaaat tgcccagtac aagttgatga tctcgacttt cttcttgccg      1380
atcatctggg ggttctggat cgtaatgacc ttgccaattg cgctctttag cgcgccgggc      1440
atcgttgttc tgatgtggct tacgatccgc tggcttgagg acttgatcca caacgcgaaa      1500
tcgatgttgt ccettttgcg attgctgttt atgacggagg ataccatgta ctcgttgaga      1560
gactaccgtc aggggctggc gcatcgtgtg cacgattttg cggtcgatca tctgaagttg      1620
cctgaggacc ctgaggttct ggtcaaggag aacaagacca agaaggtcga cagtggctgg      1680
atgggcaagt tgtcgggcag ctacttctcg atcaagagga gaagaagaaa ggactggaac      1740
gaggttatgc gattgcacga tgtttctcac tatgac                               1776
```

<210> SEQ ID NO 5
<211> LENGTH: 485
<212> TYPE: DNA
<213> ORGANISM: Mortierella alpina

<400> SEQUENCE: 5

```
ttggctgact accaaaacca gctggacttc tatcacctca aggactatcg tatcaagcaa        60
ggcaagccaa gtgcaaagat tcttatcgga cgtcttttcc aaagattctt gcttgcttgc       120
cttttgtcga ccatttgcat tcctggactg ttcctttggg cacctgtgtt tatcgccgtg       180
aagtacaaag agagtcagct taggcgcaag ggacccttgg aggacaactt ggatgaaatt       240
gcccagtaca agttgatgat ctcgactttc ttcttgccga tcatctgggg gttctggatc       300
gtaatgacct tgccaattgc gctctttagc gcgccgggca tcgttgttct gatgtggctt       360
acgatccgct ggcttgagga cttgatccac aacgcgaaat cgatgttgtc ccttttgcga       420
ttgctgtata tgacggagga taccatgtac tcgttgagag actaccgtca ggggctggag       480
catcg                                                                   485
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ctgactacca aaaccagctg gacttc                                             26
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ggcaatttca tccaagttgt cctcc                                              25
```

<210> SEQ ID NO 8

-continued

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatccatgg cccttcagat ctacga                                          26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 gtcgaccta aatgtcttttg acttggc                                         27

<210> SEQ ID NO 10
<211> LENGTH: 2154
<212> TYPE: DNA
<213> ORGANISM: Mortierella alpina
<220> FEATURE:
<221> NAME/KEY: CDS
<222> LOCATION: (1)..(2151)

<400> SEQUENCE: 10 atg gcc ctt cag atc tac gac ttc gtg tcg ttc ttc ttc act atc ctg      48
Met Ala Leu Gln Ile Tyr Asp Phe Val Ser Phe Phe Phe Thr Ile Leu
1               5                   10                  15 ctc gac atc ttc ttc agg gag att cgt ccc aga ggc gca cac aaa att      96
Leu Asp Ile Phe Phe Arg Glu Ile Arg Pro Arg Gly Ala His Lys Ile
            20                  25                  30 cca caa aaa gga ccc gtg atc ttt gtt gcc gct cct cat gcc aat cag     144
Pro Gln Lys Gly Pro Val Ile Phe Val Ala Ala Pro His Ala Asn Gln
        35                  40                  45 ttt gtc gat cct ctc gtc ttg atg cgt gag tgt ggc cgt aga gtc tca     192
Phe Val Asp Pro Leu Val Leu Met Arg Glu Cys Gly Arg Arg Val Ser
    50                  55                  60 ttc ctt gcg gcc aaa aag tct atg gac cgc cgg tgg att ggt gct atg     240
Phe Leu Ala Ala Lys Lys Ser Met Asp Arg Arg Trp Ile Gly Ala Met
65                  70                  75                  80 gca cgc tcg atg aat gcg att cct gtt gaa cgc ccg cag gat ctt gct     288
Ala Arg Ser Met Asn Ala Ile Pro Val Glu Arg Pro Gln Asp Leu Ala
                85                  90                  95 aaa gcg ggt tcg gga gtc atc aaa ctt ttg gat cgc tat ggt gat cct     336
Lys Ala Gly Ser Gly Val Ile Lys Leu Leu Asp Arg Tyr Gly Asp Pro
            100                 105                 110 ctt cga gtg aca ggt gtc ggc act aaa ttc aca aag gag cta ctt gtg     384
Leu Arg Val Thr Gly Val Gly Thr Lys Phe Thr Lys Glu Leu Leu Val
        115                 120                 125 gga gat cag ata tct ctc cca aag gac gtt ggc tcc tca gcc gtg gtc     432
Gly Asp Gln Ile Ser Leu Pro Lys Asp Val Gly Ser Ser Ala Val Val
    130                 135                 140 gag atc ata tct gat acc gag ctg att gtc aag aag gaa ttc aag gag     480
Glu Ile Ile Ser Asp Thr Glu Leu Ile Val Lys Lys Glu Phe Lys Glu
145                 150                 155                 160 ctc aag gcc ctc gaa tta ttg acc agc cct gat gga acc aag tat aaa     528
Leu Lys Ala Leu Glu Leu Leu Thr Ser Pro Asp Gly Thr Lys Tyr Lys
                165                 170                 175 tgc cta cct cac atg gac cag acg aat gta tac aaa act gtc ttt gag     576
```

```
                Cys Leu Pro His Met Asp Gln Thr Asn Val Tyr Lys Thr Val Phe Glu
                                180                 185                 190 cgc ctc aac gct gga cat tgc gtt ggc att ttc ccc gaa ggt gga tcc          624
Arg Leu Asn Ala Gly His Cys Val Gly Ile Phe Pro Glu Gly Gly Ser
            195                 200                 205 cac gat cgc gct gag atg ctg cca ttg aaa gct gga gtc acc atc atg          672
His Asp Arg Ala Glu Met Leu Pro Leu Lys Ala Gly Val Thr Ile Met
        210                 215                 220 gct ctg ggc gcg ttg gcc gcc aac cct tcg ttg gac ctc aag att gtc          720
Ala Leu Gly Ala Leu Ala Ala Asn Pro Ser Leu Asp Leu Lys Ile Val
225                 230                 235                 240 acc tgc ggc ctc aac tac ttt cat cct cat cgc ttc cgc tcg cgt gca          768
Thr Cys Gly Leu Asn Tyr Phe His Pro His Arg Phe Arg Ser Arg Ala
                245                 250                 255 gtg gtc gag ttt ggc gag cca ctg acg gtc cct cct gag ctg gtc gaa          816
Val Val Glu Phe Gly Glu Pro Leu Thr Val Pro Pro Glu Leu Val Glu
            260                 265                 270 atg tac aag cga ggc ggg gct gag aag cgt gaa gcg tgc gga aag ttg          864
Met Tyr Lys Arg Gly Gly Ala Glu Lys Arg Glu Ala Cys Gly Lys Leu
        275                 280                 285 ctg gat aca atc tat gag gct ctt cgc ggt gtc act ctc aat gca cct          912
Leu Asp Thr Ile Tyr Glu Ala Leu Arg Gly Val Thr Leu Asn Ala Pro
    290                 295                 300 gat tac gaa acg ttg atg gtc att caa gcg gcc cgt gcg ctt tac aag          960
Asp Tyr Glu Thr Leu Met Val Ile Gln Ala Ala Arg Ala Leu Tyr Lys
305                 310                 315                 320 ccc act cat cgc aag ctg cag atc tca caa gtc gtg gag ttg aac cgc         1008
Pro Thr His Arg Lys Leu Gln Ile Ser Gln Val Val Glu Leu Asn Arg
                325                 330                 335 agg ttc gtc gca gga tac atg cac ttc aag gac aac cct aaa gtc att         1056
Arg Phe Val Ala Gly Tyr Met His Phe Lys Asp Asn Pro Lys Val Ile
            340                 345                 350 gaa gcc aag gac aag gtc atg cat tac aac act caa ctt cga tac cat         1104
Glu Ala Lys Asp Lys Val Met His Tyr Asn Thr Gln Leu Arg Tyr His
        355                 360                 365 gga ctg cgc gat cat cag gtg aac att cgc aca acc agg aaa cac gct         1152
Gly Leu Arg Asp His Gln Val Asn Ile Arg Thr Thr Arg Lys His Ala
    370                 375                 380 atc ggc atg ctc atc tca cgg ctc att cag atg atc ttt ttg agt tgt         1200
Ile Gly Met Leu Ile Ser Arg Leu Ile Gln Met Ile Phe Leu Ser Cys
385                 390                 395                 400 ctg gct cta cct gga acc ctg atg aat ctt ccg gtc gct att gtc gct         1248
Leu Ala Leu Pro Gly Thr Leu Met Asn Leu Pro Val Ala Ile Val Ala
                405                 410                 415 cgt gtc atc agc aac aag aag gcc aaa gag gcg ctg gct gcc tcg aca         1296
Arg Val Ile Ser Asn Lys Lys Ala Lys Glu Ala Leu Ala Ala Ser Thr
            420                 425                 430 gtc aag att gct gga agg gat gtc ctg gct aca tgg aag ctg ctg gtc         1344
Val Lys Ile Ala Gly Arg Asp Val Leu Ala Thr Trp Lys Leu Leu Val
        435                 440                 445 gct cta gga ttg atg cct gtc ctc tac ttc aca tat tcc gtc atg gtc         1392
Ala Leu Gly Leu Met Pro Val Leu Tyr Phe Thr Tyr Ser Val Met Val
    450                 455                 460 ttt atc tat tgt ggc cgc ttc gac ata tcg ttc aag tcg cgt ctc ttg         1440
Phe Ile Tyr Cys Gly Arg Phe Asp Ile Ser Phe Lys Ser Arg Leu Leu
465                 470                 475                 480 atc gct tgg gca gca tgg gcg cta att cct ttc gta acg tat gca agc         1488
Ile Ala Trp Ala Ala Trp Ala Leu Ile Pro Phe Val Thr Tyr Ala Ser
                485                 490                 495 ata cgc ttc ggt gaa gtt ggt atc gat att ttc aaa tct atc cgc cca         1536
```

```
Ile Arg Phe Gly Glu Val Gly Ile Asp Ile Phe Lys Ser Ile Arg Pro
            500                 505                 510 ttg ttc ttg tcc atc atc cca ggt gaa gag agc acg atc aac gac ttg      1584
Leu Phe Leu Ser Ile Ile Pro Gly Glu Glu Ser Thr Ile Asn Asp Leu
            515                 520                 525 cgc aaa gcc cga gcg gaa ctc cag aag act atc acc aat ctt atc aat      1632
Arg Lys Ala Arg Ala Glu Leu Gln Lys Thr Ile Thr Asn Leu Ile Asn
            530                 535                 540 gag ctg gcg ccg cag att tat ccc gac ttt gat tcg aag cgc atc ctc      1680
Glu Leu Ala Pro Gln Ile Tyr Pro Asp Phe Asp Ser Lys Arg Ile Leu
545                 550                 555                 560 gat ccg tct cct gca gat cgc ccc agc cgc tcg gca tca ggt acc aac      1728
Asp Pro Ser Pro Ala Asp Arg Pro Ser Arg Ser Ala Ser Gly Thr Asn
            565                 570                 575 ctt gca cag aca atc ttc aac acg gcc gct cag cct ttg aac caa tgg      1776
Leu Ala Gln Thr Ile Phe Asn Thr Ala Ala Gln Pro Leu Asn Gln Trp
            580                 585                 590 cta ggc aag gac ggc cgc ttt gaa tgg gag cgc acc gag gat tcg gat      1824
Leu Gly Lys Asp Gly Arg Phe Glu Trp Glu Arg Thr Glu Asp Ser Asp
            595                 600                 605 gca gat gat gtg ttc ttc ttt ttg gac cca gca aga gga att ctt gga      1872
Ala Asp Asp Val Phe Phe Phe Leu Asp Pro Ala Arg Gly Ile Leu Gly
610                 615                 620 cgg tcg agg gcg tcg tcc tgg gga gga ggg gca ttt aca cct gcc gcc      1920
Arg Ser Arg Ala Ser Ser Trp Gly Gly Gly Ala Phe Thr Pro Ala Ala
625                 630                 635                 640 gat ggg tcg cga tcc cgg aat cgg agc agg aca agc agc ttc acg tcg      1968
Asp Gly Ser Arg Ser Arg Asn Arg Ser Arg Thr Ser Ser Phe Thr Ser
            645                 650                 655 gga cag atc cag ctt ggc gag ggc ttc aaa ctc gag gca ttg acg gaa      2016
Gly Gln Ile Gln Leu Gly Glu Gly Phe Lys Leu Glu Ala Leu Thr Glu
            660                 665                 670 ctg ccg agg gac aag cct ttt gca gag gtg acg agg cgg ctg agt gtg      2064
Leu Pro Arg Asp Lys Pro Phe Ala Glu Val Thr Arg Arg Leu Ser Val
            675                 680                 685 agc cgc atg cag aga tac ggg ttg gag ggt atg acg cgc tcg gac acg      2112
Ser Arg Met Gln Arg Tyr Gly Leu Glu Gly Met Thr Arg Ser Asp Thr
            690                 695                 700 gac gaa aac gaa ggc tct aca gcc aag tca aaa gac att tag              2154
Asp Glu Asn Glu Gly Ser Thr Ala Lys Ser Lys Asp Ile
705                 710                 715

<210> SEQ ID NO 11
<211> LENGTH: 717
<212> TYPE: PRT
<213> ORGANISM: Mortierella alpina

<400> SEQUENCE: 11

Met Ala Leu Gln Ile Tyr Asp Phe Val Ser Phe Phe Thr Ile Leu
1               5                   10                  15

Leu Asp Ile Phe Phe Arg Glu Ile Arg Pro Arg Gly Ala His Lys Ile
            20                  25                  30

Pro Gln Lys Gly Pro Val Ile Phe Val Ala Ala Pro His Ala Asn Gln
            35                  40                  45

Phe Val Asp Pro Leu Val Leu Met Arg Glu Cys Gly Arg Arg Val Ser
        50                  55                  60

Phe Leu Ala Ala Lys Lys Ser Met Asp Arg Arg Trp Ile Gly Ala Met
65                  70                  75                  80

Ala Arg Ser Met Asn Ala Ile Pro Val Glu Arg Pro Gln Asp Leu Ala
            85                  90                  95
```

```
Lys Ala Gly Ser Gly Val Ile Lys Leu Leu Asp Arg Tyr Gly Asp Pro
            100                 105                 110

Leu Arg Val Thr Gly Val Gly Thr Lys Phe Thr Lys Glu Leu Leu Val
            115                 120                 125

Gly Asp Gln Ile Ser Leu Pro Lys Asp Val Gly Ser Ser Ala Val Val
            130                 135                 140

Glu Ile Ile Ser Asp Thr Glu Leu Ile Val Lys Lys Glu Phe Lys Glu
145                 150                 155                 160

Leu Lys Ala Leu Glu Leu Leu Thr Ser Pro Asp Gly Thr Lys Tyr Lys
            165                 170                 175

Cys Leu Pro His Met Asp Gln Thr Asn Val Tyr Lys Thr Val Phe Glu
            180                 185                 190

Arg Leu Asn Ala Gly His Cys Val Gly Ile Phe Pro Glu Gly Gly Ser
            195                 200                 205

His Asp Arg Ala Glu Met Leu Pro Leu Lys Ala Gly Val Thr Ile Met
210                 215                 220

Ala Leu Gly Ala Leu Ala Ala Asn Pro Ser Leu Asp Leu Lys Ile Val
225                 230                 235                 240

Thr Cys Gly Leu Asn Tyr Phe His Pro His Arg Phe Arg Ser Arg Ala
            245                 250                 255

Val Val Glu Phe Gly Glu Pro Leu Thr Val Pro Pro Glu Leu Val Glu
            260                 265                 270

Met Tyr Lys Arg Gly Gly Ala Glu Lys Arg Glu Ala Cys Gly Lys Leu
            275                 280                 285

Leu Asp Thr Ile Tyr Glu Ala Leu Arg Gly Val Thr Leu Asn Ala Pro
            290                 295                 300

Asp Tyr Glu Thr Leu Met Val Ile Gln Ala Ala Arg Arg Leu Tyr Lys
305                 310                 315                 320

Pro Thr His Arg Lys Leu Gln Ile Ser Gln Val Val Glu Leu Asn Arg
            325                 330                 335

Arg Phe Val Ala Gly Tyr Met His Phe Lys Asp Asn Pro Lys Val Ile
            340                 345                 350

Glu Ala Lys Asp Lys Val Met His Tyr Asn Thr Gln Leu Arg Tyr His
            355                 360                 365

Gly Leu Arg Asp His Gln Val Asn Ile Arg Thr Thr Arg Lys His Ala
            370                 375                 380

Ile Gly Met Leu Ile Ser Arg Leu Ile Gln Met Ile Phe Leu Ser Cys
385                 390                 395                 400

Leu Ala Leu Pro Gly Thr Leu Met Asn Leu Pro Val Ala Ile Val Ala
            405                 410                 415

Arg Val Ile Ser Asn Lys Lys Ala Lys Glu Ala Leu Ala Ala Ser Thr
            420                 425                 430

Val Lys Ile Ala Gly Arg Asp Val Leu Ala Thr Trp Lys Leu Leu Val
            435                 440                 445

Ala Leu Gly Leu Met Pro Val Leu Tyr Phe Thr Tyr Ser Val Met Val
            450                 455                 460

Phe Ile Tyr Cys Gly Arg Phe Asp Ile Ser Phe Lys Ser Arg Leu Leu
465                 470                 475                 480

Ile Ala Trp Ala Ala Trp Ala Leu Ile Pro Phe Val Thr Tyr Ala Ser
            485                 490                 495

Ile Arg Phe Gly Glu Val Gly Ile Asp Ile Phe Lys Ser Ile Arg Pro
            500                 505                 510

Leu Phe Leu Ser Ile Ile Pro Gly Glu Glu Ser Thr Ile Asn Asp Leu
```

515                 520                 525
Arg Lys Ala Arg Ala Glu Leu Gln Lys Thr Ile Thr Asn Leu Ile Asn
530                 535                 540

Glu Leu Ala Pro Gln Ile Tyr Pro Asp Phe Asp Ser Lys Arg Ile Leu
545                 550                 555                 560

Asp Pro Ser Pro Ala Asp Arg Pro Ser Arg Ser Ala Ser Gly Thr Asn
                565                 570                 575

Leu Ala Gln Thr Ile Phe Asn Thr Ala Ala Gln Pro Leu Asn Gln Trp
            580                 585                 590

Leu Gly Lys Asp Gly Arg Phe Glu Trp Glu Arg Thr Glu Asp Ser Asp
        595                 600                 605

Ala Asp Asp Val Phe Phe Phe Leu Asp Pro Ala Arg Gly Ile Leu Gly
610                 615                 620

Arg Ser Arg Ala Ser Ser Trp Gly Gly Gly Ala Phe Thr Pro Ala Ala
625                 630                 635                 640

Asp Gly Ser Arg Ser Arg Asn Arg Ser Arg Thr Ser Ser Phe Thr Ser
                645                 650                 655

Gly Gln Ile Gln Leu Gly Glu Gly Phe Lys Leu Glu Ala Leu Thr Glu
            660                 665                 670

Leu Pro Arg Asp Lys Pro Phe Ala Glu Val Thr Arg Arg Leu Ser Val
        675                 680                 685

Ser Arg Met Gln Arg Tyr Gly Leu Glu Gly Met Thr Arg Ser Asp Thr
        690                 695                 700

Asp Glu Asn Glu Gly Ser Thr Ala Lys Ser Lys Asp Ile
705                 710                 715

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctagaatgg caccteccaa cactattg                                         28

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagcttttac ttcttgaaaa agaccacgtc                                       30

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tctagaatgg ctgctgctcc cagtgtgag                                        29

<210> SEQ ID NO 15
<211> LENGTH: 29

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagcttttac tgtgccttgc ccatcttgg                                   29

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctagaatgg agtcgattgc gcaattcc                                    28

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagctcttac tgcaacttcc ttgccttctc                                  30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctagaatgg gtgcggacac aggaaaaacc                                  30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagcttttac tcttccttgg gacgaagacc                                  30

<210> SEQ ID NO 20
<211> LENGTH: 1203
<212> TYPE: DNA
<213> ORGANISM: Mortierella alpina

<400> SEQUENCE: 20
atggcacctc ccaacactat tgatgccggt ttgacccagc gccatatcag cacctcggcc      60
gccccaacct ctgccaagcc cgccttcgag cgcaactacc agctccctga gttcaccatc     120
aaggagatcc gtgagtgcat ccctgcacac tgctttgagc gctccggtct ccgtggtctt     180
tgccacgttg ctattgatct gacctgggcc tcgctcttgt tcctggctgc gacccagatc     240
gacaagttcg agaaccccttt gatccgctac ttggcctggc ctgcgtattg gatcatgcag     300
```

| | |
|---|---:|
| ggtattgttt gcaccggtat ctgggtattg gcacacgaat gtggtcatca gtccttctcg | 360 |
| acctccaaga cccttaacaa cactgtcggc tggatcttgc actcgatgct cttggtccct | 420 |
| taccactcct ggagaatctc gcactcgaag caccacaagg ccactggcca catgaccaag | 480 |
| gaccaggtct tgttcccaa gacccgctct caggttggct tgccccccaa ggagaatgtt | 540 |
| gcagttgccg ttcaggagga ggatatgtcc gtgcacctgg atgaggaggc ccccattgtg | 600 |
| actttgttct ggatggtgat tcagttcctg ttcggatggc ctgcgtacct tattatgaac | 660 |
| gcctctggtc aagactatgg ccgctggacc tcgcacttcc acacctactc tcctatcttt | 720 |
| gagcccccgca acttttttcga cattatcatt tcggatctcg gtgtgttggc tgctcttggt | 780 |
| accttgatct acgcctccat gcagctctcg ctcttgaccg tgaccaagta ctacattgtc | 840 |
| ccctacttgt ttgtcaactt ctggttggtc ctgatcacct tcttgcagca caccgaccct | 900 |
| aagctgcccc attaccgtga gggtgcctgg aacttccagc gtggagccct ctgcaccgtt | 960 |
| gaccgctcgt tcggcaagtt cttggaccat atgttccacg gcattgtcca tacccatgta | 1020 |
| gcccatcact tgttctcgca gatgccgttc taccatgctg aggaagccac ccatcatctc | 1080 |
| aagaaactgc tgggagagta ctacgtctat gacccatcgc cgattgttgt tgcggtctgg | 1140 |
| aggtcgttcc gtgaatgccg attcgtggaa gaccatggag acgtggtctt tttcaagaag | 1200 |
| taa | 1203 |

<210> SEQ ID NO 21
<211> LENGTH: 1374
<212> TYPE: DNA
<213> ORGANISM: Mortierella alpina

<400> SEQUENCE: 21

| | |
|---|---:|
| atggctgctg ctcccagtgt gaggacgttt actcgggccg agattttgaa tgccgaggcc | 60 |
| ctgaatgagg gcaagaagga tgccgaggca ccctttctga tgatcattga caacaaggtg | 120 |
| tacgatgtcc gcgagtttgt ccctgatcat cccggtggaa gtgtgattct cacgcacgtt | 180 |
| ggcaaggacg gcactgacgt cttttgacact ttccaccccg aggctgcttg ggagactctt | 240 |
| gccaactttt acgttggtga tattgatgag agcgatcgtg ccatcaagaa tgatgacttt | 300 |
| gcggccgagg ttcgcaagct gcgcaccttg ttccagtccc ttggctacta cgactcgtcc | 360 |
| aaggcatact atgccttcaa ggtctcgttc aacctctgca tctggggctt gtcgactttc | 420 |
| attgttgcca gtggggccga gacctcgacc ctcgccaacg tgctctcggc tgcgctcttg | 480 |
| ggtctcttct ggcagcagtg cggatggttg gcgcacgact ttttgcacca ccaggtcttc | 540 |
| caggaccgtt tctggggtga tcttttcggc gccttcttgg aggtgtctg ccagggtttc | 600 |
| tcgtcctcct ggtggaagga caagcacaac actcaccacg ctgctcccaa cgtccacggc | 660 |
| gaggatcccg acattgacac tcaccctctg ttgacctgga gtgagcatgc tctggagatg | 720 |
| ttctcggatg ttcctgacga ggagctgacc cgtatgtggt cgcgcttcat ggtcctcaac | 780 |
| cagacctggt tctacttccc cattctctcg tttgcccgtc tgtcctggtg cctccagtcc | 840 |
| attatgcttt ttctgcccaa cggtcaggcc acaagccct ctggagcgcg tgtgcccatt | 900 |
| tcgttggtcg agcagctgtc tctggctatg cactggacct ggtacctcgc caccatgttc | 960 |
| ctgttcatta aggatcccgt caacatgatt gtgtactttt tggtgtcgca ggctgtttgc | 1020 |
| ggcaacttgt tggcgattgt gttctcgctc aaccacaacg gcatgcctgt gatctccaag | 1080 |
| gaggaagcgg tcgatatgga cttcttcacc aagcagatca tcacgggtcg tgatgttcac | 1140 |
| cctggtctgt ttgccaactg gttcacgggt ggattgaact accagattga gcaccacttg | 1200 |

```
ttcccttcga tgccccgcca caacttttca aagatccagc ctgctgtcga gactttgtgc    1260
aaaaagtacg gtgtccgata ccataccact ggtatgatcg agggaactgc agaggtcttt    1320
agccgtttga acgaggtctc caaggcggcc tccaagatgg gcaaggcaca gtaa          1374
```

<210> SEQ ID NO 22
<211> LENGTH: 957
<212> TYPE: DNA
<213> ORGANISM: Mortierella alpina

<400> SEQUENCE: 22

```
atggagtcga ttgcgcaatt cctcccctca aagatgccgc aagatctgtt tattgacctt     60
gcaagggcca tcggtgtcca ggccgcaccc tatgtcgacc ctctcgaggc agcgcttgtg    120
gcccaggccg agaagttctt ccccacggtc gttcatcaca cgcgcggctt tttggtcgcg    180
gtcgagtcac ccttggcccg tgagctgccc ttgatgaacc ccttccacgt gctgttgatc    240
gcgctcgctt acttggtcac ggtctttgtg ggcatgcaga tcatgaagaa ctttgaacgg    300
ttcgaggtca agacgttctc gctcttccac aacttttgtc tggtctcgat cagtgcctac    360
atgtgcggcg ggatcttgta cgaggcttac caggccaact atggactgtt tgagaacgcg    420
gccgatcata ccgtccaggg tcttcctatg gccaagatga tctggctctt ctacttctcc    480
aagatcatgg agtttgtcga caccatgatc atggtcctta agaagaacaa ccgccagatc    540
tcgttcttgc acgtctacca ccacagctcc atcttcacca tctggtggtt ggtcaccttt    600
gttgcaccca atggtgaagc ctacttctcg gctgcgttga actcgttcat ccacgtgatc    660
atgtacggct actacttcct gtccgccttg gcttcaagc aggtgtcgtt catcaagttc    720
tacatcacgc gttcgcagat gacgcagttc tgcatgatgt cgatccagtc ctcctgggac    780
atgtatgcca tgaaggtgct tggccgcccc ggataccct tcttcatcac cgccctgctt    840
tggttctaca tgtggaccat gctcggactc ttctacaact tctacagaaa gaacgccaag    900
ttggccaagc aggccaagat cgatgctgcc aaggagaagg caaggaagtt gcagtaa       957
```

<210> SEQ ID NO 23
<211> LENGTH: 1341
<212> TYPE: DNA
<213> ORGANISM: Mortierella alpina

<400> SEQUENCE: 23

```
atgggtgcgg acacaggaaa aaccttcacc tggcaagaac tcgcggcgca taacaccgag     60
gacagcctcc ttttggctat ccgtggcaat gtatacgatg tcacaaagtt cttgagccgt    120
catcctggtg gaacggatac tctcttgctc ggagctggcc gagatgtcac tccggttttt    180
gagatgtacc acgagtttgg agctgcagag gctatcatga agagtactga tgttggcaca    240
ctggtctcaa atgagttgcc catcttccca gagccaacgg tgttccataa gaccatcaag    300
ggcagagttg aggcatactt taaggaccgg aacatggatt ccaagaacag accagagatc    360
tggggacgat atgctctcat cttggatcc ttgatcgcct cttactacgc gcagctcttt    420
gtaccgttcg tggtcgaacg tacatggctc caggtggtgt ttgctatcat catgggatt     480 gcgtgcgcgc aagtcggatt gaaccctctt cacgatgcct cccactttc agtgacccac    540 aaccccaccg tttggaagat tctcggagcc acgcacgact ttttcaacgg agcatcgtat    600
ctcgtgtgga tgtaccaaca tatgctcggc catcatccct ataccaacat tgctggagct    660
gatcccgatg tgtcgacctc tgagcccgat gttcgtcgta tcaagcccaa ccaaaagtgg    720
ttcgtcaacc acatcaacca gcacatgttt gttcctttcc tgtacggact gctggcgttc    780
```

```
aaggtgcgca tccaggacat caacatcttg tactttgtca agaccaatga cgccattcgt      840
gtcaacccca tctcgacttg gcacaccgtc atgttctggg gcggaaaggc cttctttgtc      900
tggtaccgct tgatcgttcc tatgcagtat ctgcccctga gcaaggtgtt gctcttgttt      960
accgtcgcag acatggtctc ttcttactgg ctggcgctga ccttccaggc gaaccacgtt     1020
gttgaggagg ttcagtggcc attgcctgat gagaatggaa tcatccaaaa ggattgggca     1080
gccatgcagg tcgagactac tcaggattac gcccacgatt cgcacctctg gaccagcatc     1140
acgggcagct tgaactacca agccgttcat catctgttcc gaacgtttc ccagcatcac      1200 taccctgata tcctggctat catcaaggac acctgcagcg agtacaaggt gccatacctc     1260
gtcaaggata ccttttggca agcgtttgct tcacatttgg agcacttgcg tgtgcttggt     1320
cttcgtccca aggaagagta a                                                1341

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cacaccacac attcaacatc                                                    20

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggcaatttca tccaagttgt cctcc                                              25

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgactacca aaaccagctg gacttc                                             26

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcatcccgc aaacacacac                                                    20
```